United States Patent
Alvarez et al.

(10) Patent No.: US 10,709,872 B2
(45) Date of Patent: *Jul. 14, 2020

(54) REENTRY CATHETER AND METHOD THEREOF

(71) Applicant: The Spectranetics Corporation, Colorado Springs, CO (US)

(72) Inventors: Jeffery B. Alvarez, Redwood, CA (US); Christine Godleski, Colorado Springs, CO (US); Wade A. Bowe, Colorado Springs, CO (US); Rob Carver, Colorado Springs, CO (US); Paola A. Dwelle, Colorado Springs, CO (US); Jeff Lindstrom, Rancho Santa Margarita, CA (US); David S. Nevrla, Friendswood, TX (US); Shahriar Matin, Colorado Springs, CO (US); Matthew M. Magee, Monument, CO (US)

(73) Assignee: THE SPECTRANETICS CORPORATION, Colorado Springs, CO (US)

(*) Notice: Subject to any disclaimer, the term of this patent is extended or adjusted under 35 U.S.C. 154(b) by 10 days.

This patent is subject to a terminal disclaimer.

(21) Appl. No.: 15/725,089

(22) Filed: Oct. 4, 2017

(65) Prior Publication Data

US 2018/0043134 A1    Feb. 15, 2018

Related U.S. Application Data

(63) Continuation of application No. 14/128,050, filed as application No. PCT/US2012/045011 on Jun. 29, 2012, now Pat. No. 9,814,862.

(Continued)

(51) Int. Cl.
    *A61M 25/01*    (2006.01)
    *A61M 25/00*    (2006.01)
    (Continued)

(52) U.S. Cl.
    CPC ..... *A61M 25/0172* (2013.01); *A61B 17/3423* (2013.01); *A61M 25/003* (2013.01);
    (Continued)

(58) Field of Classification Search
    CPC .......... A61B 2017/22094; A61B 2017/22095; A61B 2017/22001; A61B 2017/22038;
    (Continued)

(56) References Cited

U.S. PATENT DOCUMENTS

| 3,853,004 A | 12/1974 | Cebuliak et al. |
| 4,227,293 A | 10/1980 | Taylor |

(Continued)

FOREIGN PATENT DOCUMENTS

| EP | 0166212 A2 | 1/1986 |
| JP | 2006181370 A | 7/2006 |

(Continued)

OTHER PUBLICATIONS

Belli et al., "Peripheral Vascular Occlusions: Mechanical Recanalization with a Metal Laser Probe after Guide Wire Dissection," Radiology, vol. 176: 539-541, Aug. 1990.

(Continued)

*Primary Examiner* — Lauren P Farrar
*Assistant Examiner* — James D Ponton

(57) ABSTRACT

Embodiments of the invention are directed towards a rapid exchange catheter configured for insertion into a subintimal space and crossing an occlusion in a subintimal space. The catheter includes a proximal end, a distal end, a first lumen configured to receive a first wire, the first lumen extending longitudinally through a least a lateral port of the catheter, (Continued)

and a second lumen having at least a portion distal of the lateral port and extending through at least the distal end of the catheter. The catheter also includes an exchange port, arranged on an exterior portion of the catheter configured to receive a second wire and second rapid exchange port in communication with the second lumen. Moreover, other embodiments of the invention are directed towards methods for using the rapid exchange catheter to cross an obstruction in a vessel, e.g., a total or partial occlusion, in a subintimal space.

18 Claims, 38 Drawing Sheets

Related U.S. Application Data

(60) Provisional application No. 61/503,477, filed on Jun. 30, 2011, provisional application No. 61/533,019, filed on Sep. 9, 2011, provisional application No. 61/533,024, filed on Sep. 9, 2011.

(51) Int. Cl.
A61B 17/34 (2006.01)
A61B 17/22 (2006.01)

(52) U.S. Cl.
CPC .... *A61M 25/0074* (2013.01); *A61M 25/0108* (2013.01); *A61M 25/0194* (2013.01); *A61B 2017/22044* (2013.01); *A61B 2017/22095* (2013.01); *A61M 25/005* (2013.01); *A61M 25/0069* (2013.01); *A61M 2025/0004* (2013.01); *A61M 2025/0008* (2013.01); *A61M 2025/0037* (2013.01); *A61M 2025/0079* (2013.01); *A61M 2025/018* (2013.01); *A61M 2025/0183* (2013.01); *A61M 2025/0197* (2013.01)

(58) Field of Classification Search
CPC .. A61B 2017/00252; A61B 2017/1205; A61B 2017/018; A61B 17/22; A61B 17/12118; A61B 17/12109; A61B 17/3423; A61B 2017/22044; A61M 25/104; A61M 25/005; A61M 25/0052; A61M 25/0053; A61M 2025/018; A61M 25/0172; A61M 25/003; A61M 25/0068; A61M 25/0069; A61M 25/0071; A61M 25/0194; A61M 25/0074; A61M 25/0018; A61M 2025/0004; A61M 2025/0037; A61M 2025/007; A61M 2025/0008
See application file for complete search history.

(56) References Cited

U.S. PATENT DOCUMENTS

| | | |
|---|---|---|
| 4,552,554 A | 11/1985 | Gould et al. |
| 4,664,112 A | 5/1987 | Kensey et al. |
| 4,712,547 A | 12/1987 | Bonnet |
| 4,774,949 A | 10/1988 | Fogarty |
| 4,784,636 A | 11/1988 | Rydell |
| 4,926,858 A | 5/1990 | Gifford et al. |
| 4,994,067 A | 2/1991 | Summers |
| 5,047,040 A | 9/1991 | Simpson et al. |
| 5,053,044 A | 10/1991 | Mueller et al. |
| 5,066,288 A | 11/1991 | Deniega et al. |
| 5,092,872 A | 3/1992 | Segalowitz |
| 5,100,426 A | 3/1992 | Nixon |
| 5,104,382 A | 4/1992 | Brinkerhoff et al. |
| 5,135,531 A | 8/1992 | Shiber |
| 5,234,450 A | 8/1993 | Segalowitz |
| 5,242,461 A | 9/1993 | Kortenbach et al. |
| 5,279,551 A | 1/1994 | James |
| 5,287,861 A | 2/1994 | Wilk |
| 5,308,354 A | 5/1994 | Zacca et al. |
| 5,334,211 A | 8/1994 | Shiber |
| 5,336,176 A | 8/1994 | Yoon |
| 5,391,177 A | 2/1995 | Schwartz |
| 5,409,019 A | 4/1995 | Wilk |
| 5,413,581 A | 5/1995 | Goy |
| 5,423,846 A | 6/1995 | Fischell |
| 5,429,497 A | 7/1995 | Yamada et al. |
| 5,443,443 A | 8/1995 | Shiber |
| 5,443,497 A | 8/1995 | Venbrux |
| 5,512,044 A | 4/1996 | Duer |
| 5,536,251 A | 7/1996 | Evard et al. |
| 5,558,665 A | 9/1996 | Kieturakis |
| 5,596,990 A | 1/1997 | Yock et al. |
| 5,601,588 A | 2/1997 | Tonomura et al. |
| 5,628,761 A | 5/1997 | Rizik |
| 5,632,755 A | 5/1997 | Nordgren et al. |
| 5,643,298 A | 7/1997 | Nordgren et al. |
| 5,649,941 A | 7/1997 | Lary |
| 5,651,781 A | 7/1997 | Grace |
| 5,658,311 A | 8/1997 | Baden |
| 5,690,664 A | 11/1997 | Sauer et al. |
| 5,695,469 A | 12/1997 | Segal |
| 5,702,390 A | 12/1997 | Austin et al. |
| 5,724,977 A | 3/1998 | Yock et al. |
| 5,728,129 A | 3/1998 | Summers |
| 5,746,758 A | 5/1998 | Nordgren et al. |
| 5,776,154 A | 7/1998 | Taylor et al. |
| 5,830,222 A | 11/1998 | Makower |
| 5,836,868 A | 11/1998 | Ressemann et al. |
| 5,841,893 A | 11/1998 | Ishikawa et al. |
| 5,879,305 A | 3/1999 | Yock et al. |
| 5,902,263 A | 5/1999 | Patterson et al. |
| 5,935,108 A | 8/1999 | Katoh et al. |
| 5,938,671 A | 8/1999 | Katoh et al. |
| 5,941,893 A | 8/1999 | Saadat |
| 5,951,567 A | 9/1999 | Javier et al. |
| 5,972,019 A | 10/1999 | Engelson et al. |
| 6,024,730 A | 2/2000 | Pagan |
| 6,027,514 A | 2/2000 | Stine et al. |
| 6,066,149 A | 5/2000 | Samson et al. |
| 6,080,171 A | 6/2000 | Keith et al. |
| 6,080,175 A | 6/2000 | Hogendijk |
| 6,081,738 A | 6/2000 | Hinohara et al. |
| 6,096,054 A | 8/2000 | Wyzgala et al. |
| 6,155,264 A | 12/2000 | Ressemann et al. |
| 6,190,353 B1 | 2/2001 | Makower et al. |
| 6,196,230 B1 | 3/2001 | Hall et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,235,000 B1 | 5/2001 | Milo et al. |
| 6,238,406 B1 | 5/2001 | Ellis et al. |
| 6,302,875 B1 | 10/2001 | Makower et al. |
| 6,402,778 B2 | 6/2002 | Wang |
| 6,419,659 B1 | 7/2002 | Phelps et al. |
| 6,419,685 B2 | 7/2002 | Di Caprio et al. |
| 6,432,129 B2 | 8/2002 | DiCaprio |
| 6,475,226 B1 | 11/2002 | Belef et al. |
| 6,488,693 B2 | 12/2002 | Gannoe et al. |
| 6,506,178 B1 | 1/2003 | Schubart et al. |
| 6,506,200 B1 | 1/2003 | Chin |
| 6,506,201 B2 | 1/2003 | Di Caprio et al. |
| 6,511,458 B2 | 1/2003 | Milo et al. |
| 6,533,753 B1 | 3/2003 | Haarstad et al. |
| 6,533,755 B2 | 3/2003 | Adams |
| 6,544,230 B1 | 4/2003 | Flaherty et al. |
| 6,569,129 B1 | 5/2003 | Holmes et al. |
| 6,579,302 B2 | 6/2003 | Duerig et al. |
| 6,589,274 B2 | 7/2003 | Stiger et al. |
| 6,592,568 B2 | 7/2003 | Campbell |
| 6,596,005 B1 | 7/2003 | Kanz et al. |
| 6,602,225 B2 | 8/2003 | Eidenschink et al. |
| 6,655,386 B1 | 12/2003 | Makower et al. |
| 6,663,577 B2 | 12/2003 | Jen et al. |
| 6,676,667 B2 | 1/2004 | Mareiro et al. |

(56) References Cited

U.S. PATENT DOCUMENTS

| | | | |
|---|---|---|---|
| 6,702,777 B2 | 3/2004 | Haim et al. |
| 6,719,725 B2 | 4/2004 | Milo et al. |
| 6,736,841 B2 | 5/2004 | Musbach et al. |
| 6,796,963 B2 | 9/2004 | Carpenter et al. |
| 6,808,531 B2 | 10/2004 | Lafontaine et al. |
| 6,818,001 B2 | 11/2004 | Wulfman et al. |
| 6,881,216 B2 | 4/2005 | Di Caprio et al. |
| 6,890,348 B2 | 5/2005 | Sydney et al. |
| 6,923,827 B2 | 8/2005 | Campbell et al. |
| 6,942,681 B2 | 9/2005 | Johnson |
| 7,004,173 B2 | 2/2006 | Sparks et al. |
| 7,056,323 B2 | 6/2006 | Mareiro et al. |
| 7,083,639 B2 | 8/2006 | Guinan et al. |
| 7,137,990 B2 | 11/2006 | Hebert et al. |
| 7,147,655 B2 | 12/2006 | Chermoni |
| 7,172,575 B2 | 2/2007 | El-Nounou et al. |
| 7,172,621 B2 | 2/2007 | Theron |
| 7,175,607 B2 | 2/2007 | Lim et al. |
| 7,179,270 B2 | 2/2007 | Makower |
| 7,201,770 B2 | 4/2007 | Johnson et al. |
| 7,226,472 B2 | 6/2007 | Pederson et al. |
| 7,273,485 B2 | 9/2007 | Simpson et al. |
| 7,314,588 B2 | 1/2008 | Blankenship |
| 7,329,267 B2 | 2/2008 | Weber |
| 7,344,557 B2 | 3/2008 | Yadin |
| 7,399,291 B2 | 7/2008 | Vo et al. |
| 7,476,214 B2 | 1/2009 | Sydney et al. |
| 7,553,324 B2 | 6/2009 | Andreas et al. |
| 7,572,270 B2 | 8/2009 | Johnson |
| 7,604,621 B2 | 10/2009 | Eidenschink |
| 7,632,288 B2 | 12/2009 | Wu |
| 7,951,186 B2 | 5/2011 | Eidenschink et al. |
| 8,956,376 B2 | 2/2015 | Alvarez et al. |
| 8,998,936 B2 | 4/2015 | Alvarez et al. |
| 9,814,862 B2 * | 11/2017 | Alvarez | A61M 25/0074 |
| 2001/0000041 A1 | 3/2001 | Selmon et al. |
| 2001/0014821 A1 | 8/2001 | Juman et al. |
| 2001/0029387 A1 | 10/2001 | Wolf et al. |
| 2001/0031981 A1 | 10/2001 | Evans et al. |
| 2001/0034547 A1 | 10/2001 | Hall et al. |
| 2002/0103459 A1 | 8/2002 | Sparks et al. |
| 2003/0014100 A1 | 1/2003 | Maria Meens et al. |
| 2003/0032999 A1 | 2/2003 | Huang |
| 2003/0109809 A1 | 6/2003 | Jen et al. |
| 2003/0171799 A1 | 9/2003 | Lee et al. |
| 2003/0236542 A1 | 12/2003 | Makower |
| 2004/0044392 A1 | 3/2004 | Von Oepen |
| 2004/0170782 A1 | 9/2004 | Wang et al. |
| 2004/0181252 A1 | 9/2004 | Boyle et al. |
| 2004/0230219 A1 | 11/2004 | Roucher |
| 2005/0004649 A1 | 1/2005 | Mistry et al. |
| 2005/0021002 A1 | 1/2005 | Deckman et al. |
| 2005/0027248 A1 | 2/2005 | Suzuki et al. |
| 2005/0038382 A1 | 2/2005 | Miller et al. |
| 2005/0049574 A1 | 3/2005 | Petrick et al. |
| 2005/0049672 A1 | 3/2005 | Murphy |
| 2005/0055078 A1 | 3/2005 | Campbell |
| 2005/0059938 A1 | 3/2005 | Malisch |
| 2005/0075711 A1 | 4/2005 | Neary |
| 2005/0085845 A1 | 4/2005 | Hilaire et al. |
| 2005/0085889 A1 | 4/2005 | Sundar |
| 2005/0090853 A1 | 4/2005 | Duchamp |
| 2005/0090888 A1 | 4/2005 | Hines et al. |
| 2005/0096722 A1 | 5/2005 | Lootz et al. |
| 2005/0102020 A1 | 5/2005 | Grayzel et al. |
| 2005/0107819 A1 | 5/2005 | Sater |
| 2005/0118370 A1 | 6/2005 | Varma et al. |
| 2005/0119731 A1 | 6/2005 | Brucker et al. |
| 2005/0131444 A1 | 6/2005 | Ricci |
| 2005/0171478 A1 | 8/2005 | Selmon et al. |
| 2005/0209559 A1 | 9/2005 | Thornton et al. |
| 2005/0271844 A1 | 12/2005 | Mapes et al. |
| 2005/0273021 A1 | 12/2005 | Burgermeister |
| 2005/0273149 A1 | 12/2005 | Tran et al. |
| 2005/0273153 A1 | 12/2005 | Clerc et al. |
| 2005/0277979 A1 | 12/2005 | Dorros et al. |
| 2005/0278011 A1 | 12/2005 | Peckham |
| 2005/0288629 A1 | 12/2005 | Kunis |
| 2006/0009737 A1 | 1/2006 | Whiting et al. |
| 2006/0009832 A1 | 1/2006 | Fisher |
| 2006/0015133 A1 | 1/2006 | Grayzel et al. |
| 2006/0025843 A1 | 2/2006 | Gurm et al. |
| 2006/0030922 A1 | 2/2006 | Dolan |
| 2006/0030924 A1 | 2/2006 | Van Der Leest et al. |
| 2006/0047336 A1 | 3/2006 | Gale et al. |
| 2006/0074476 A1 | 4/2006 | Holman et al. |
| 2006/0085058 A1 | 4/2006 | Rosenthal et al. |
| 2006/0106448 A1 | 5/2006 | Shaked |
| 2006/0129179 A1 | 6/2006 | Weber et al. |
| 2006/0135909 A1 | 6/2006 | Holman et al. |
| 2006/0173440 A1 | 8/2006 | Lamson et al. |
| 2006/0184186 A1 | 8/2006 | Noone |
| 2006/0235458 A1 | 10/2006 | Belson |
| 2006/0276749 A1 | 12/2006 | Selmon et al. |
| 2007/0021685 A1 | 1/2007 | Oepen et al. |
| 2007/0093780 A1 | 4/2007 | Kugler et al. |
| 2007/0208368 A1 | 9/2007 | Katoh et al. |
| 2007/0250036 A1 | 10/2007 | Volk et al. |
| 2007/0265563 A1 | 11/2007 | Heuser |
| 2007/0276419 A1 * | 11/2007 | Rosenthal | A61B 17/32002 |
| | | | 606/159 |
| 2008/0097247 A1 | 4/2008 | Eskuri |
| 2008/0114390 A1 | 5/2008 | Guinan |
| 2008/0125748 A1 * | 5/2008 | Patel | A61M 25/0084 |
| | | | 604/509 |
| 2008/0140101 A1 | 6/2008 | Carley et al. |
| 2008/0154172 A1 | 6/2008 | Mauch |
| 2008/0228171 A1 * | 9/2008 | Kugler | A61B 17/221 |
| | | | 604/529 |
| 2008/0234717 A1 | 9/2008 | Bruszewski |
| 2008/0243065 A1 | 10/2008 | Rottenberg et al. |
| 2008/0243067 A1 | 10/2008 | Rottenberg et al. |
| 2008/0249465 A1 | 10/2008 | Ryder et al. |
| 2009/0088685 A1 | 4/2009 | Kugler et al. |
| 2009/0093829 A1 | 4/2009 | Melsheimer et al. |
| 2009/0124857 A1 | 5/2009 | Viola |
| 2009/0157162 A1 * | 6/2009 | Chow | A61F 2/95 |
| | | | 623/1.11 |
| 2009/0171430 A1 | 7/2009 | Bairn et al. |
| 2009/0209910 A1 | 8/2009 | Kugler et al. |
| 2009/0234378 A1 | 9/2009 | Escudero et al. |
| 2009/0270888 A1 | 10/2009 | Patel et al. |
| 2010/0063534 A1 | 3/2010 | Kugler et al. |
| 2010/0286626 A1 | 11/2010 | Petersen et al. |
| 2010/0317973 A1 | 12/2010 | Nita |
| 2013/0006167 A1 | 1/2013 | Alvarez et al. |
| 2015/0119910 A1 | 4/2015 | Alvarez et al. |
| 2015/0165163 A1 | 6/2015 | Alvarez et al. |

FOREIGN PATENT DOCUMENTS

| | | |
|---|---|---|
| WO | 9713471 A1 | 4/1997 |
| WO | 1997013463 A1 | 4/1997 |
| WO | 2008005888 A2 | 1/2008 |
| WO | 2013003757 A2 | 1/2013 |

OTHER PUBLICATIONS

Bolia et al., "Percutaneous Extraluminal (Subintimal) Recanalization of a Brachial Artery Occlusion Following Cardiac Catheterization," CardioVascular and Intemventional Radiology, vol. 19, pp. 184-186, 1996.

Bolia et al., "Percutaneous Transluminal Angioplasty of Occlusions of the Femoral and Popliteal Arteries by Subintimal Dissection," CarioVascular and Interventional Radiology, vol. 13, pp. 357-363, 1990.

Bolia et al., "Recanalisation of Femora-Popliteal Occlusions: Improving Success Rate by Subintimal Recanalisation," letter to editor, CarioVascular and Interventional Radiology, date unknown.

Bolia et al., "Recanalization of Iliac Artery Occlusion by Subintimal Using the Ipsilateral and the Contralateral Approach," Clinical Radiology, vol. 52, pp. 684-687, 1997.

(56) References Cited

OTHER PUBLICATIONS

Bolia et al., "Subintimal and Intraluminal Recanalisation of Occluded Crural Arteries by Percutaneous Balloon Angioplasty," European Journal of Vascular Surgery, vol. 8, pp. 214-219, 1994.

Braun, "Guide Wire-assisted Placement of Non-End-Hole Nasoenteric Feeding Tubes," letter to editor, Radiology, p. 606, Feb. 2000.

Glasby et al., "Subintimal angioplasty," C212, 2008, vol. VI(1), pp. 12-16.

Heenan et al., "Clinics in Interventional Radiology: Percutaneous Transluminal Angioplasty by a Retrigrade Subintimal Transpopliteal Approach," Clinical Radiology, vol. 49, pp. 824-828, 1994.

International Search Report and Written Opinion issued in PC/US2012/052858 dated Jan. 25, 2013, 10 pages.

International Search Report and Written Opinion issued in PCT/US2012/045011 dated Jan. 7, 2013, 10 pages.

International Search Report and Written Opinion issued in PCT/US2012/052852 dated Nov. 2, 2012, 8 pages.

Mathis et al., "Use of a Guide Catheter as a Temporary Stent during Microcatheter Intervention," American Journal of Neuroradiology, vol. 19, pp. 932-933, May 1998.

Miyayama et al., "Use of a Catheter with a Large Side Hole for Selective Catheterization of the Inferior Phrenic Artery," Journal of Vascular Interventional Radiology, vol. 12, pp. 497-499, Apr. 2001.

Murphy et al., "Use of a Curved Needle for True Lumen Re-entry during Subintimal Iliac Artery Revascularlization," Journal of Vascular and Interventional Radiology, vol. 8, pp. 633-636, Jul.-Aug. 1997.

Nasim et al., "Intentional Extraluminal Recanalisation of the Femoropopliteal Segment Following Perforation During Percutaneous Transluminal Angioplasty," European Journal of Vascular and Endovascular Surgery, vol. 12, pp. 246-249, Aug. 1996.

Niydahl et al., "Subintimal Angioplasty of Infrapopliteal Occlusions in Critically Ischaemic Limbs," European Journal of Vascular and Endovascular Surgery, vol. 14, pp. 212-216, Sep. 1997.

Office Action issued for U.S. Appl. No. 13/229,378 dated Sep. 6, 2013, 10 pages.

Office Action issued in U.S. Appl. No. 13/229,392 dated Nov. 7, 2013, 10 pages.

Reekers et al., "Percutaneous intentional extraluminal (subintimal) recanalization: How to do it yourself," European Journal of Radiology, vol. 28, pp. 192-198, 1998.

Reekers et al., "Percutaneous Intentional Extraluminal Recanalisation of the Femoropopliteal Artery," European Journal of Vascular Surgery, vol. 8, pp. 723-728, Nov. 1994.

U.S. Appl. No. 15/227,800 entitled Reentry Catheter and Method Thereof, filed Aug. 3, 2016.

Won et al., "Microcatheter Placement through a Side Hole Created in a 5-F Catheter into Proximal Subclavian Arterial Branches Causing Hemoptysis," Journal of Vascular and Inverventional Radiology, vol. 15, No. 8, pp. 881-884, Aug. 2004.

U.S. Appl. No. 14/128,050, filed Jun. 17, 2014.

* cited by examiner

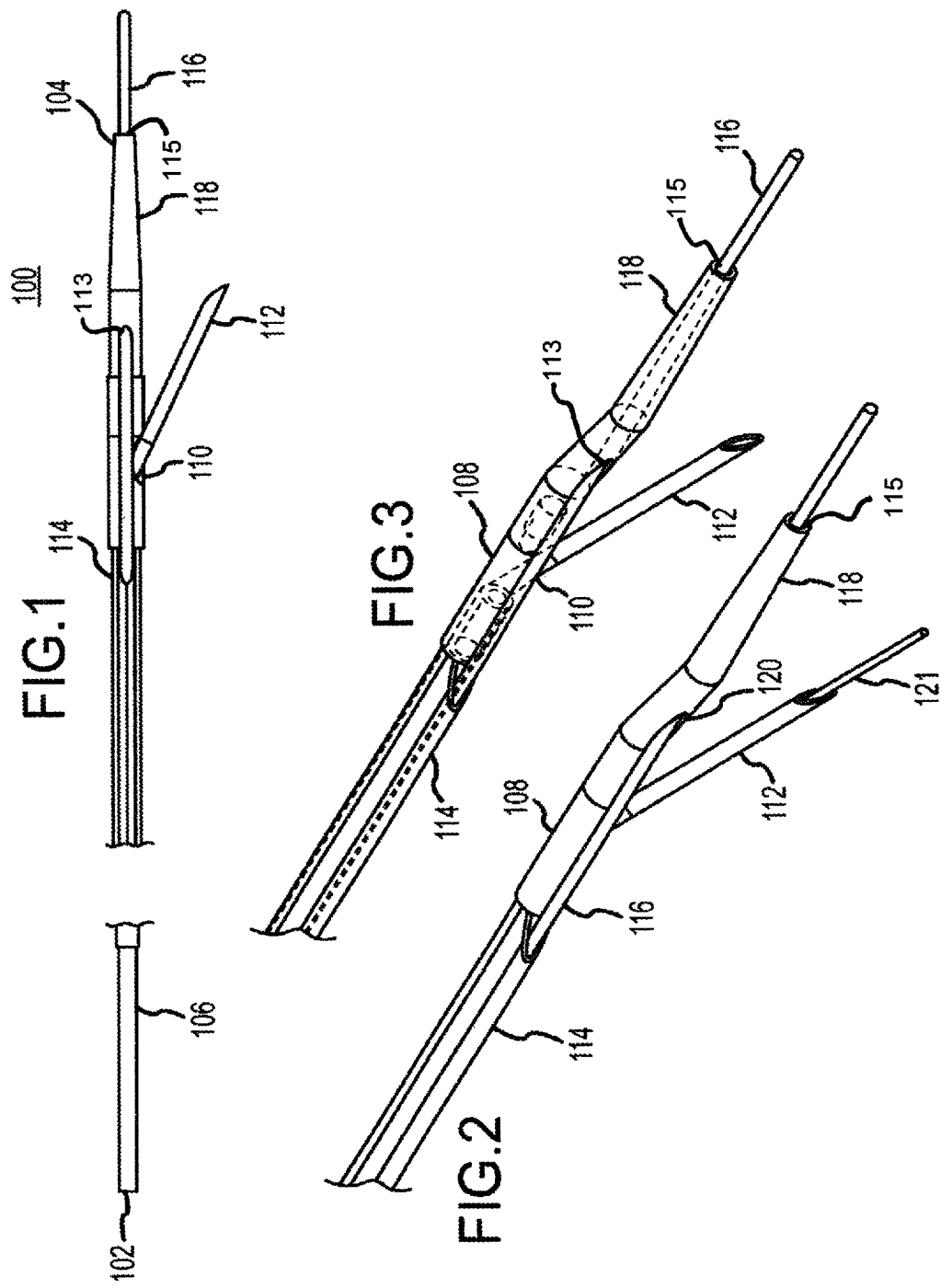

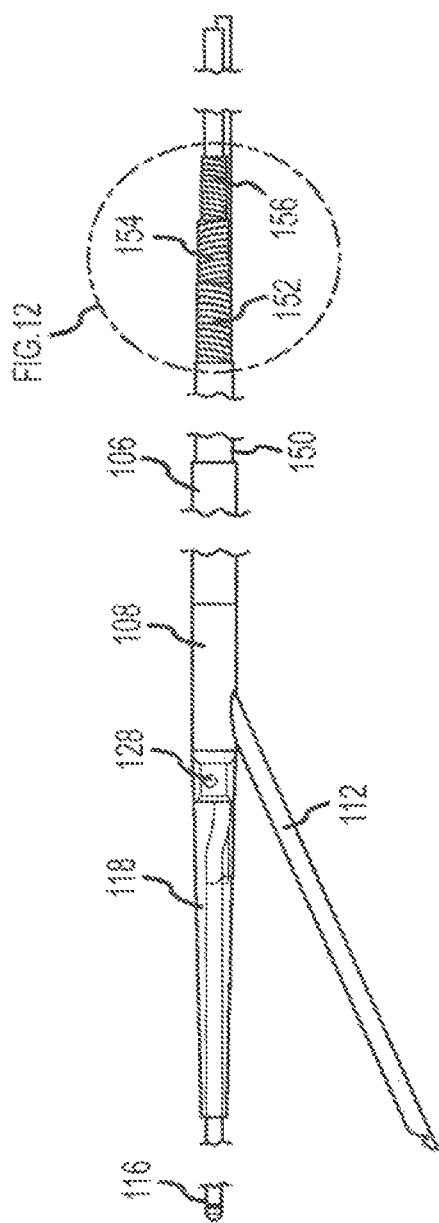

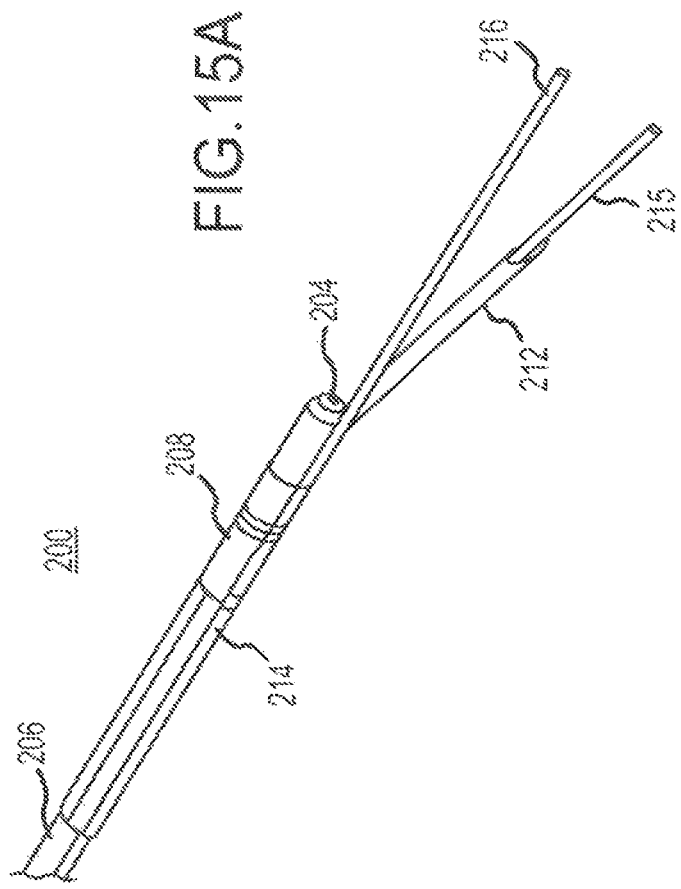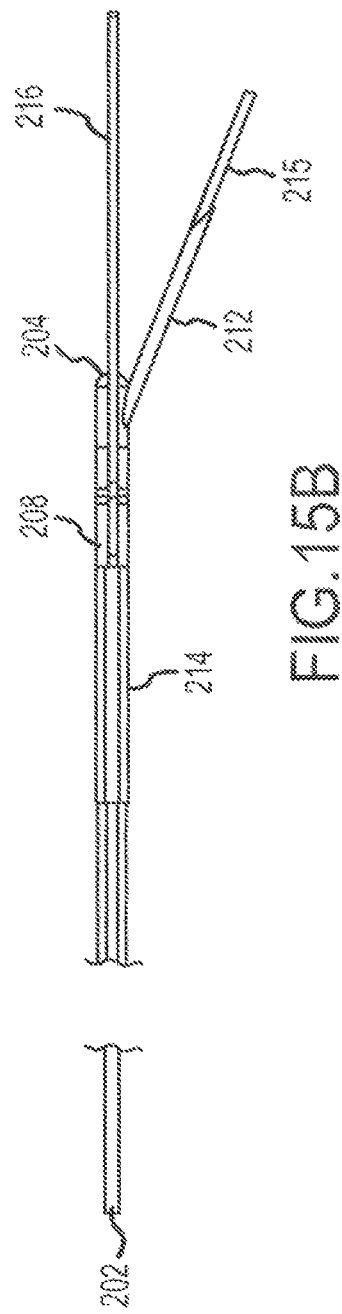

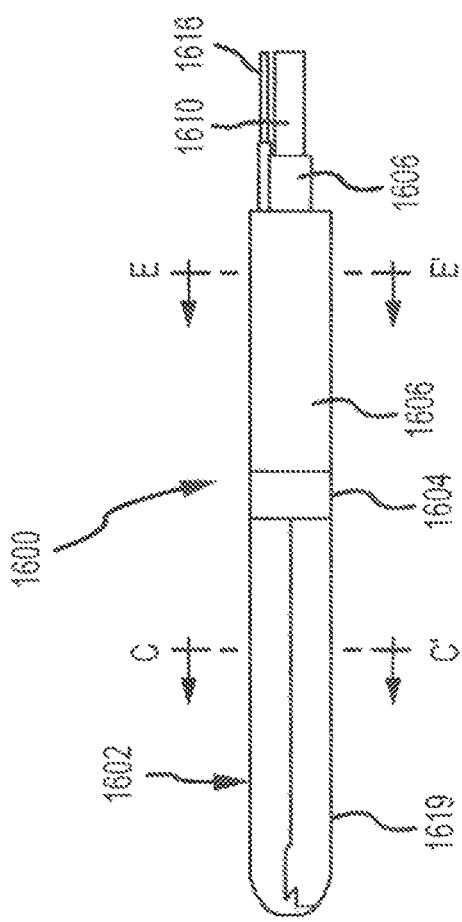
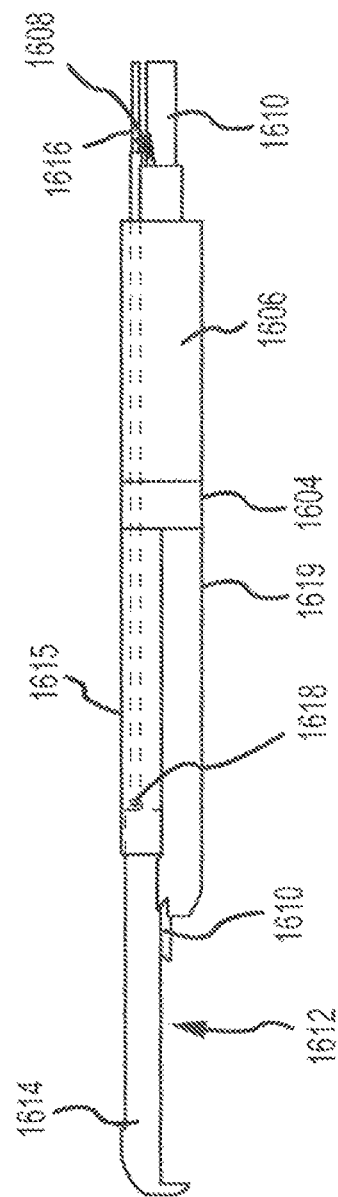

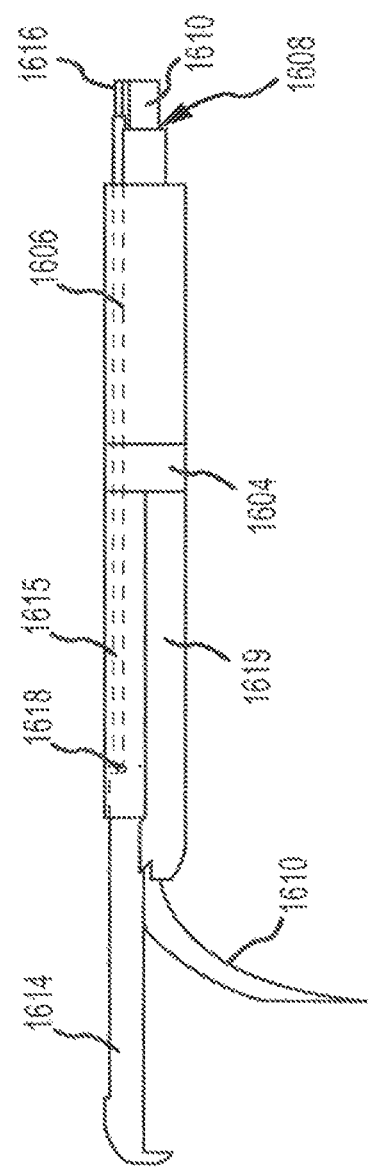

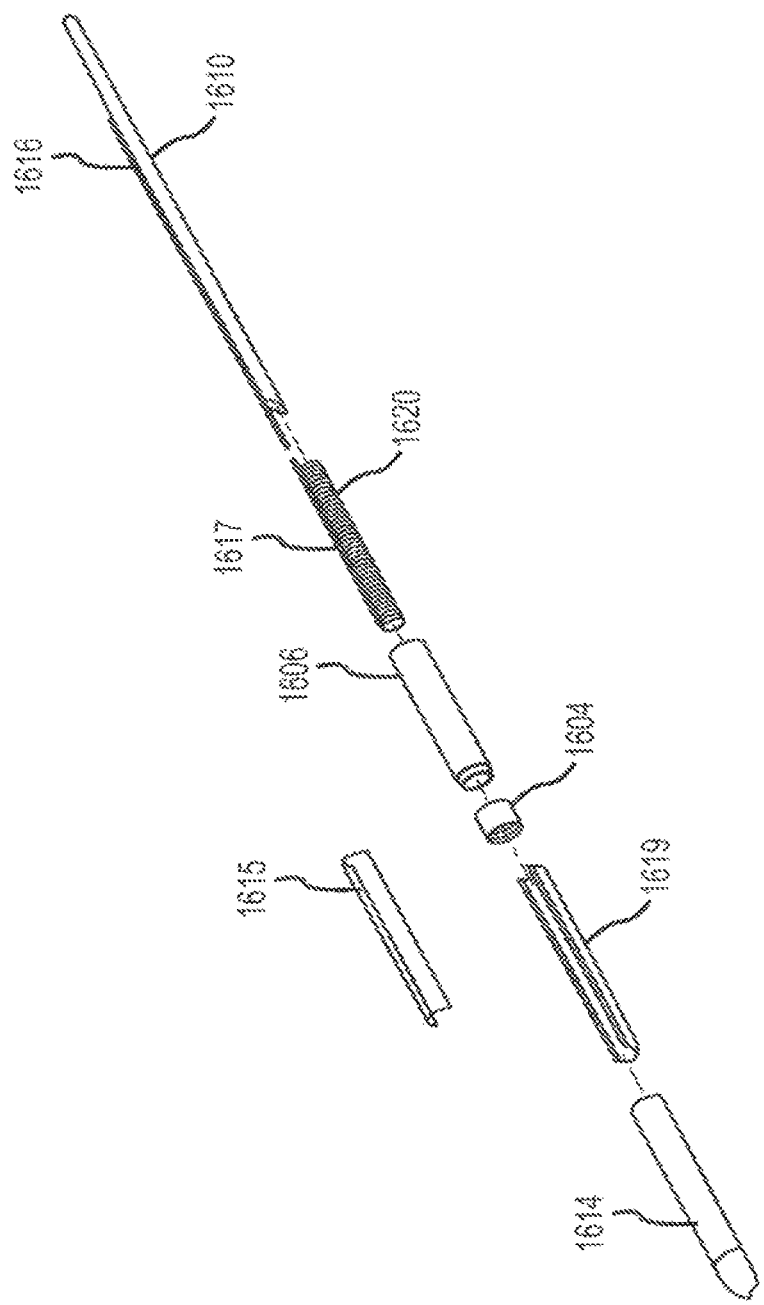

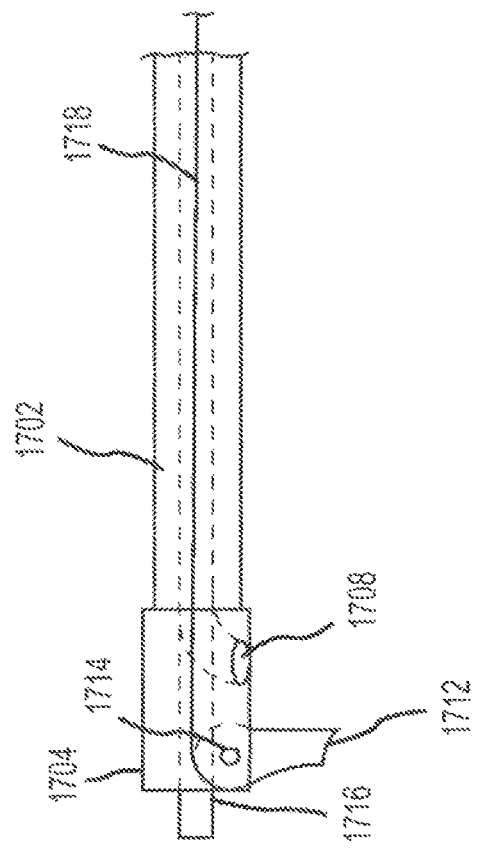
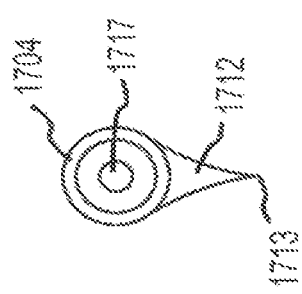
FIG. 17E
FIG. 17D

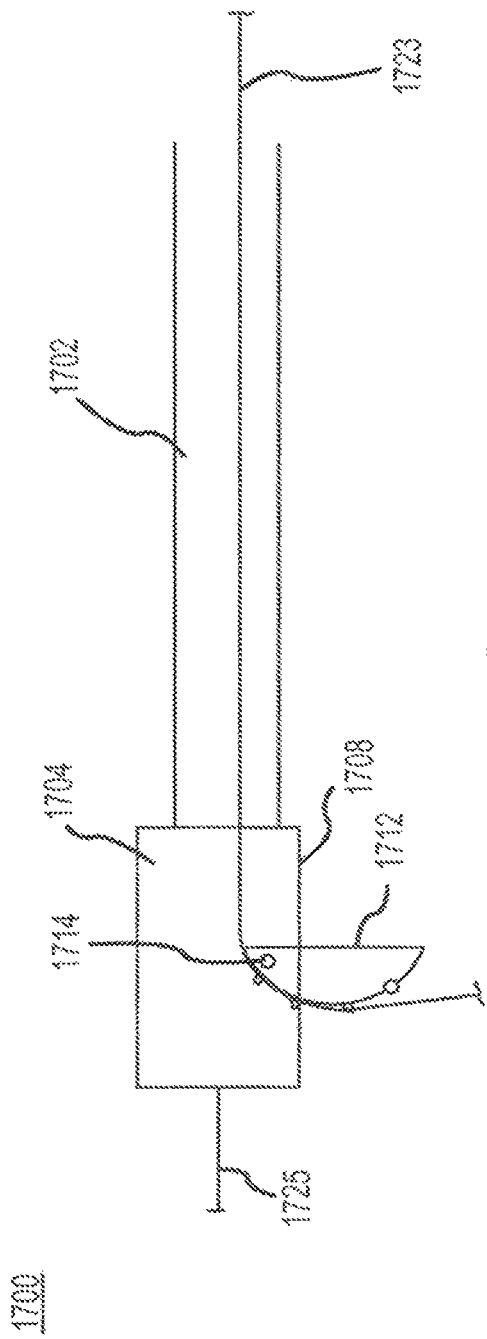
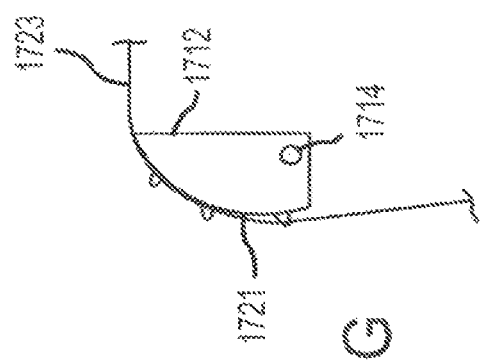
FIG. 17F
FIG. 17G

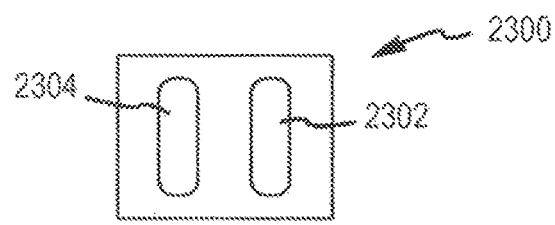
FIG.23A
FIG.23B    FIG.23C    FIG.23D
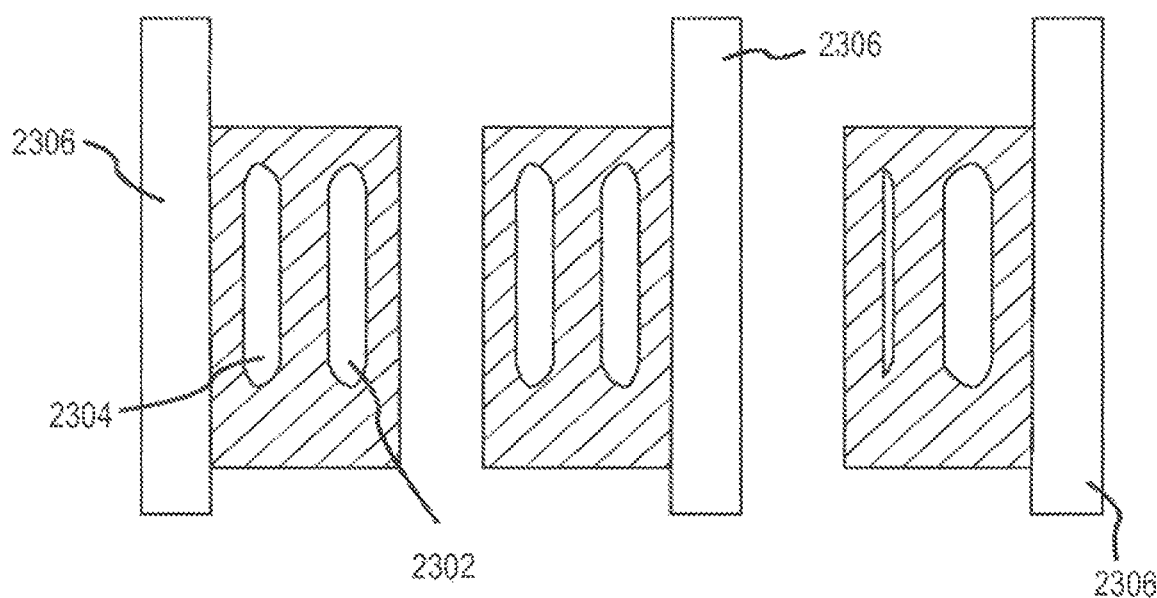

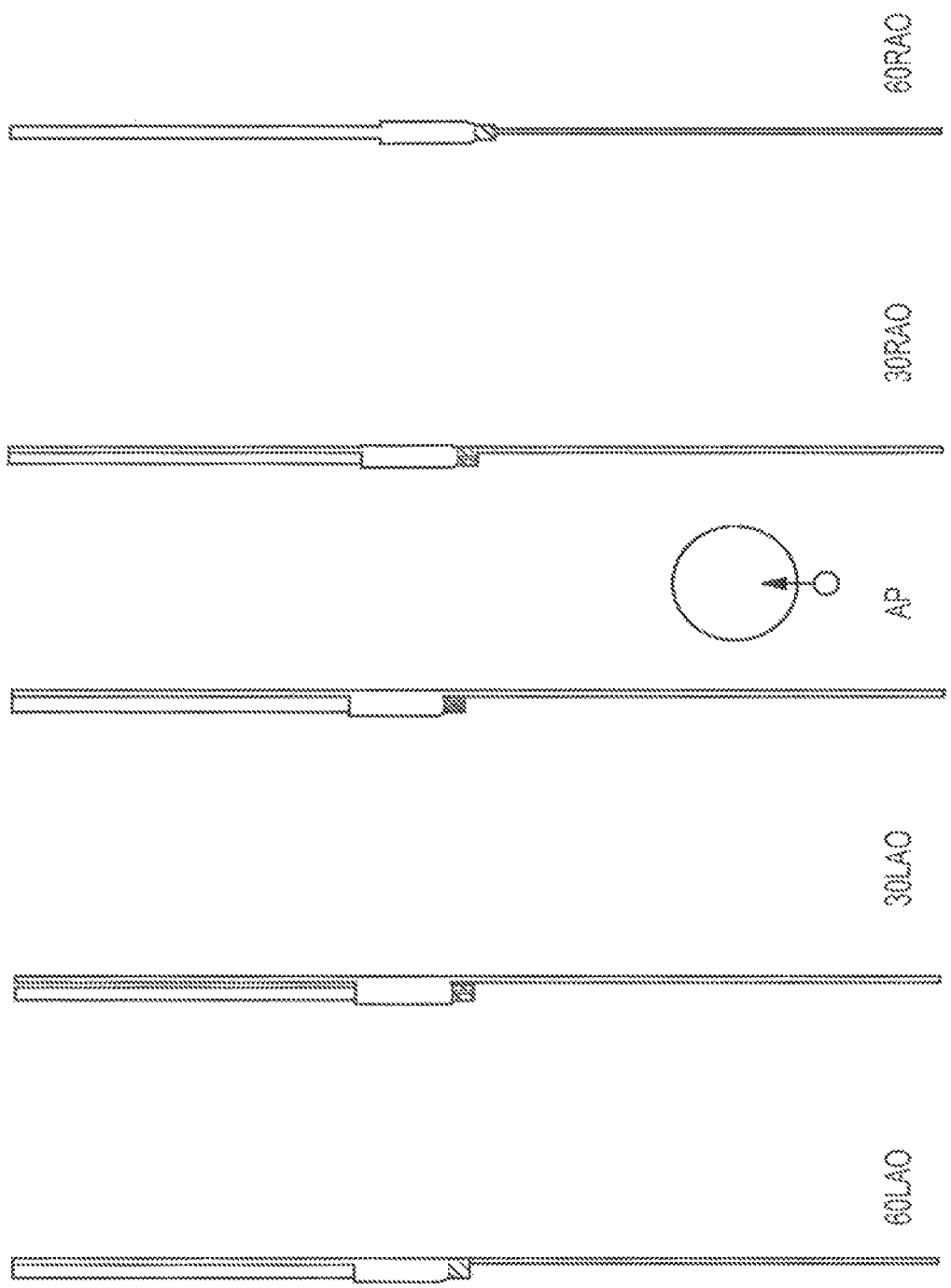

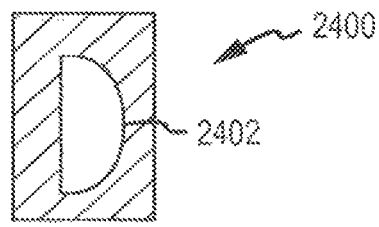
FIG.24A
FIG.24B  FIG.24C  FIG.24D
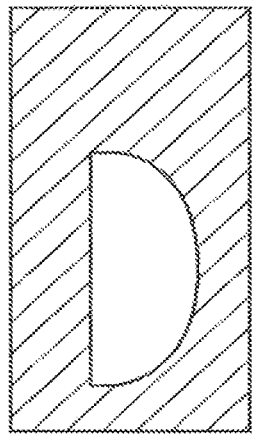 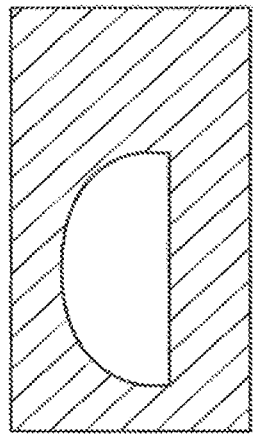 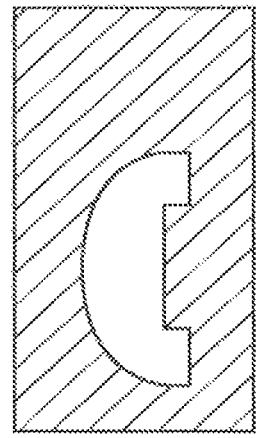
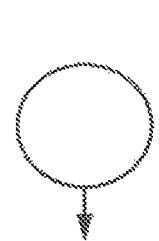 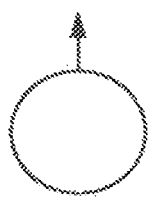 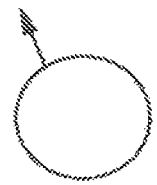

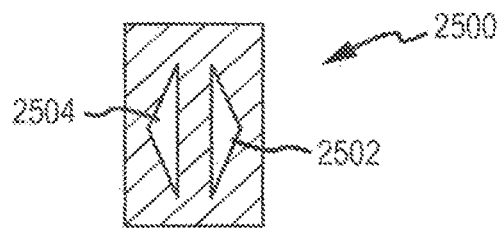
FIG.25A
FIG.25B  FIG.25C  FIG.25D
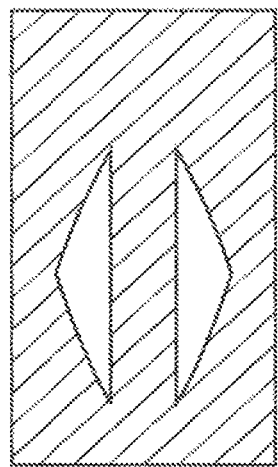 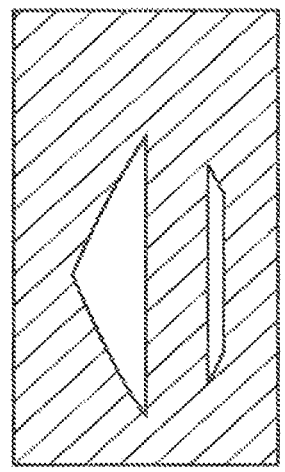 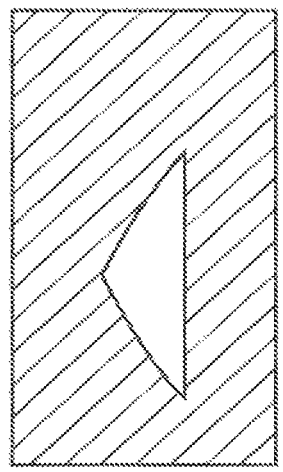
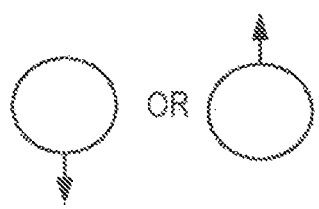 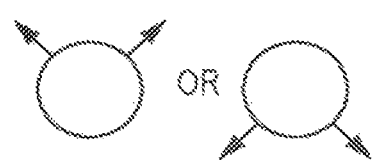 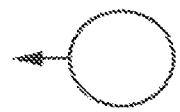

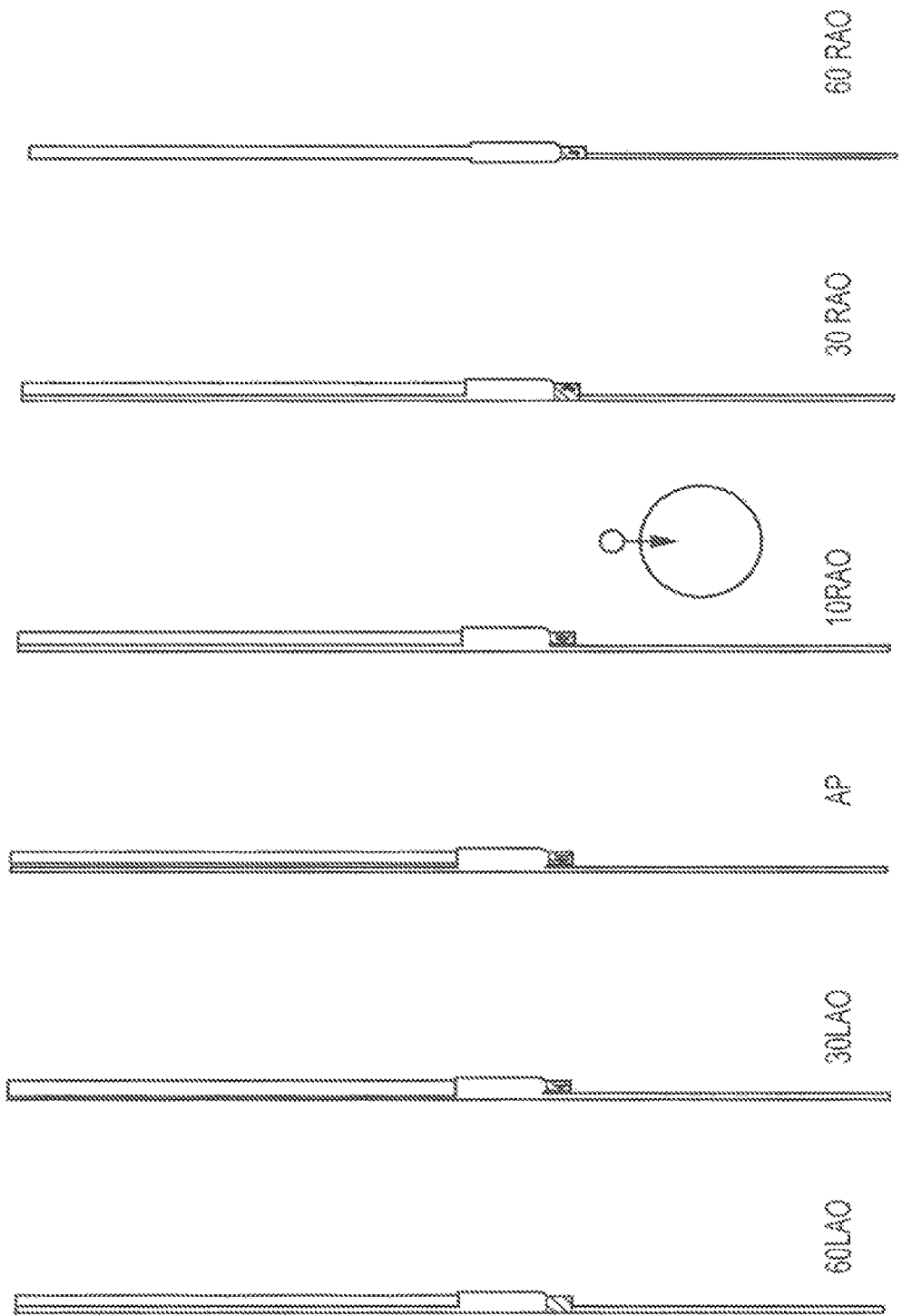

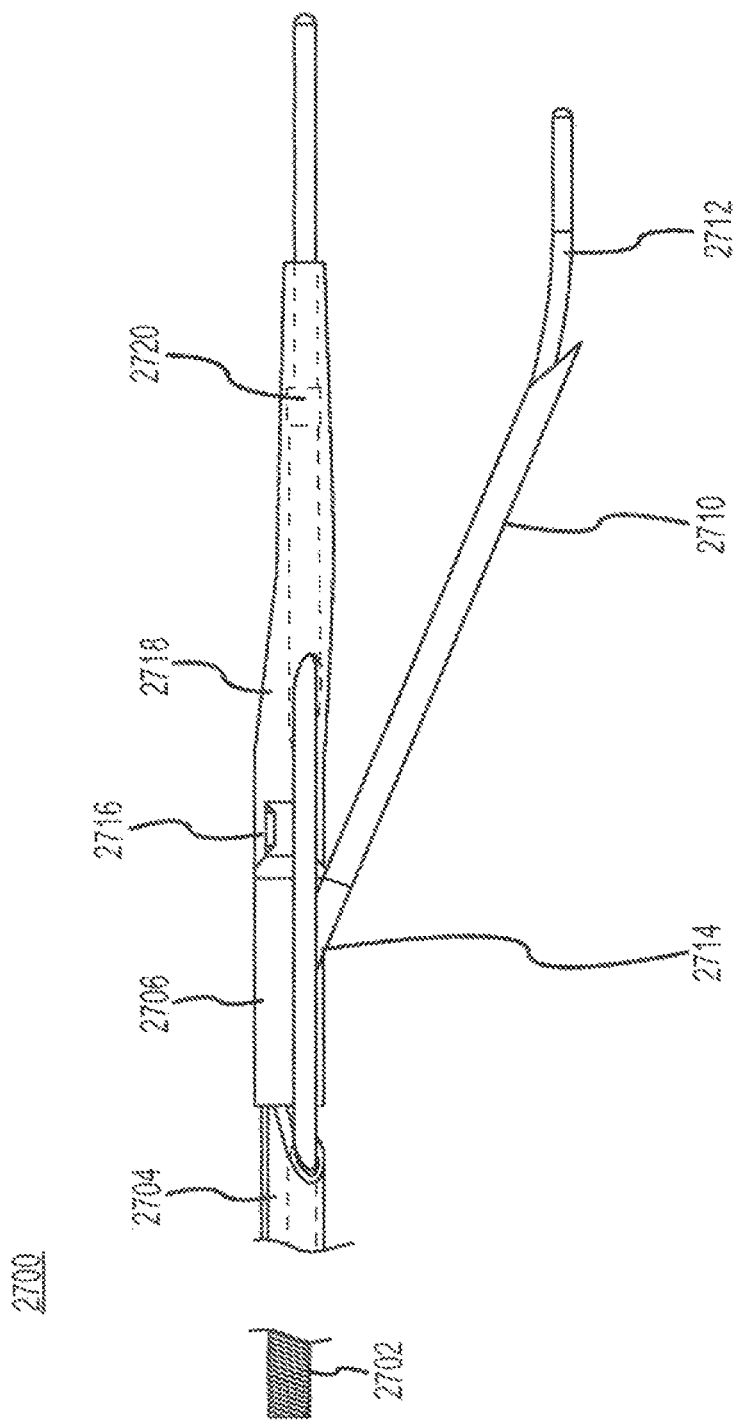

REENTRY CATHETER AND METHOD THEREOF

This application is a continuation of U.S. patent application Ser. No. 14/128,050, filed Jun. 17, 2014, now U.S. Pat. No. 9,814,862, which is a national stage application under 35 U.S.C. 371 of PCT Application No. PCT/US2012/045011, having an international filing date of Jun. 29, 2012, which designated the United States, which claims the benefit of U.S. Provisional Patent Application No. 61/503,477, filed on Jun. 30, 2011, U.S. Provisional Patent Application No. 61/533,024, filed on Sep. 9, 2011, and U.S. Provisional Patent Application No. 61/533,019, filed on Sep. 9, 2011, each of the foregoing applications is hereby incorporated by reference for all purposes as if fully set forth herein.

BACKGROUND OF THE INVENTION

Field of the Invention

The invention generally relates to a method and apparatus for crossing an obstruction in a tubular member, and more particularly to a medical device and method for crossing an occlusion or partial occlusion in a subintimal or interstitial space of the vasculature.

Discussion of the Related Art

Atherosclerosis is a common human ailment arising from the deposition of a fatty-like substance, such as atheroma, or plaque on the walls of major blood vessels. These deposits occur within the peripheral arterial system which feeds the limbs of the body and also occur within the coronary arterial system which feeds the heart. These deposits accumulate in localized areas, narrow the vascular lumen, and eventually cause restriction of normal blood flow. In some cases, the deposits result in a chronic partial or total occlusion. Such restriction can lead to serious health risks including critical limbischaemia, peripheral arterial disease, and heart attack. If blood flow cannot be adequately restored through surgical or endovascular intervention, the probability of limb amputation and other patient injury increases dramatically.

A need exists for a device and method for crossing an obstruction in a tubular member, and more particularly to a medical device and method for crossing of an occlusion.

SUMMARY OF THE INVENTION

Accordingly, the invention is directed to a medical device and method thereof that substantially obviates one or more of the problems due to limitations and disadvantages of the related art.

An advantage of the invention is improved stability of the device when oriented within the blood vessel through minimization of the effect of stored torsional forces within the shaft.

Another advantage of the invention is improved stability and control of the distal tip during deployment of the cannula or interventional wire upon reentry from the subintimal space to the vessel lumen thereby preventing the device from backing out or further separating the intima from the adventitia.

Yet another advantage of the invention is improved visualization regarding the direction in which the cannula or interventional wire will deploy thereby preventing dissection or other vessel injury upon reentry.

Another advantage of the invention is improved tracking and control, thereby allowing a physician or operator to re-enter the vessel lumen at their preferred location close to the distal end of the total occlusion.

Still another advantage of the invention is the reduction in the force required to cross the subintimal layer during device reentry into the true vessel lumen due to the articulating cannula or sharp member.

Yet another advantage of the invention is the reduction in the overall required size of the device since a long rigid element is not needed at the distal tip to support large reentry forces.

Still another advantage of the invention is improved stability and control of the distal tip during deployment of the cannula or interventional wire upon reentry from the subintimal space to the true vessel lumen thereby preventing the device from backing out or further separating the intima from the adventitia.

Another advantage of the invention is the reduction in the overall size of the device since a long, permanent distal tip extension is not required to support reentry forces.

Yet another advantage of the invention is the reduced tip stiffness profile which provides improved tracking through tortuous anatomy compared to prior art.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a method for crossing an obstruction in a blood vessel is provided. The method includes advancing a first wire into an interstitial space of a vessel. Next, a rapid exchange catheter is advanced into the subintimal space with the aid of the first wire. That is, the rapid exchange catheter is advanced along the first wire with the aid of the exchange port. A second wire is advanced down a central lumen of the rapid exchange catheter and the second wire is advanced through a lateral port of the rapid exchange catheter system into the lumen of the blood vessel. In a preferred embodiment, reentry into the lumen of a vessel is accomplished at a location immediately distal to the total occlusion. It is noted that other locations may also be used for reentry. Preferably, a cannula is configured to exit the lateral port and into the true lumen of the vessel from the subintimal space prior to the second wire being advanced through the lateral port. However, a cannula need not be utilized.

Another aspect of the invention is directed towards a catheter system that includes a catheter having a proximal end, a distal end, lateral port, and a first lumen configured to received a first wire. The first lumen extends longitudinally though at least the lateral port of the catheter. The catheter also includes a second lumen having a portion extending distally of the lateral port and also extending through at least the distal end of the catheter. Preferably, the first and second lumens are discontinuous with each other. The catheter further includes an exchange port, e.g., an RX port, arranged along an exterior portion of the catheter body and configured to receive a second wire. The RX port permits the second wire to extend through the RX port and through the second lumen out the distal end of the catheter.

Yet another aspect of the invention is directed towards a reentry catheter for use in forming a pathway in an interstitial space of an artery. The reentry catheter includes a catheter body having a proximal end, a distal end, at least one lumen, and at least on lateral port. An exchange port is arranged on at least a distal portion of the catheter body, the exchange port includes at least one lumen configured to receive a guidewire and the catheter body is configured to track over the guidewire to a treatment site. A rotating reentry cutter is arranged near the distal end of the catheter with a pivot point coupled to a rigid distal catheter portion and at least one sharp leading edge. The distal end of the rotating reentry cutter is configured to deploy through at least one lateral port of the catheter from a first stowed position to a second deployed position with a leading edge of the rotating reentry cutter positioned to penetrate the interstitial space of an artery. A tether, coil, linkage or other suitable control mechanism is coupled to a portion of the rotating reentry cutter to apply and eccentric force which subsequently causes the rotating reentry cutter to rotate from a first stowed position to a second deployed position. Application of an opposite eccentric load causes the rotary reentry cutter to return from the extended or deployed position to a fully retracted position within the rigid distal portion. The reentry catheter is designed to be utilized with a conventional guidewire and/or a conventional guidewire with a micro-support catheter. The reentry catheter can include an internal ramp or wedge, or the like, to guide the crossing support catheter or guidewire out a distal port or out the lateral port from a first position within the subintimal space to a second position within the vessel true lumen.

In another embodiment of the invention, the curvature of the rotating reentry cutter can be used as a deflecting guide to direct the reentry crossing guidewire from a first position within the subintimal space, through the lateral port, along the curvature of the cutter, through the laceration zone created by the cutter, and into a second position within the vessel true lumen. In an alternative embodiment, the wire can be retained in a channel, retaining rings, or the like along the outer most distal edge of the rotating reentry device when it is in a deployed position to serve as a guide to direct the wire through the laceration created by the rotating reentry cutter.

Another embodiment of the invention is directed towards a method of crossing an obstruction in a blood vessel with a reentry catheter in a subintimal space of a vessel. The method includes advancing a first guidewire into a lumen of the vessel towards the obstruction in the vessel. Advancing the first guidewire into the subintimal space of the vessel to a location distal of the obstruction and advancing a catheter comprising a rotating reentry cutter over the guidewire to a location where a port of the catheter is at a location distal of the obstruction. The reentry catheter may be advanced in an over the guidewire configuration through a lumen of the catheter body or via an exchange port. The method further includes application of an eccentric force to the rotating reentry cutter which rotates the sharp edge from a protective stowed position to a second deployed position such that the sharp leading edge penetrates at least partially through the subintimal vessel layers. Actuation of the deployment force may be performed through a handle control actuation mechanism near the proximal end of the device as known in the art. Next, a push or pull force is applied to the reentry catheter causing the sharp edge of the rotating reentry cutter to lacerate the subintimal layers of the vessel. The laceration can be controlled by controls, as known in the art, such that the catheter moves proximally a controlled or fixed distance. A wire, internal support catheter, or interventional device is then deployed through either a distal port or through the lateral port from within the subintimal space of the vessel to a second location within a true lumen of the vessel. Next, the method may include returning the rotary reentry cutter from the second location to the first location and removing the reentry catheter and support catheter, if using, from the vessel.

In yet another embodiment, a second wire or the original wire in an over the wire configuration, is advanced down a central lumen of a reentry cannula that is configured to deploy through at least one port created by the separation of the distal portion of the catheter to gain access to a vessel true lumen from a subintimal space.

In still another embodiment, the operator activates the reentry cannula through either a push or pull mechanism which subsequently either extends a split portion of the distal tip of the catheter distally or retracts a second split portion of the distal tip proximally to provide stability in both the lateral and axial directions upon reaction to the penetration force of cannula re-entry into the vessel true lumen. Through this preferred embodiment, reentry into the true lumen of a vessel is accomplished at a location immediately distal to the total occlusion. It is noted that other locations may also be used for reentry. This embodiment provides for a longer distal extension than is present in currently available in the related art.

In still another embodiment, the reentry cannula is configured to exit the at least one port created by the separation of the distal portion of the catheter and cross into the true lumen of the vessel from the subintimal space prior to advancement of an intervention wire through the distal port.

Another aspect of the invention is directed towards a catheter system that includes a catheter having a proximal end, a distal end, a split catheter distal tip, at least one lumen, and at least one port exposed upon separation of the split catheter distal tip. At least one lumen extends longitudinally through the at least one lateral port of the catheter. The catheter includes a reentry cannula which is configured to gain access to a vessel true lumen from a subintimal space. The reentry cannula is configured to penetrate the vessel layers adjacent to the at least one lateral port. The reentry cannula is configured to have a hollow portion to receive a supplemental treatment device, such as, an interventional guide wire.

Yet another aspect of the invention is directed towards a reentry catheter for using in forming a pathway in an interstitial space of an artery. The reentry catheter includes a catheter body including a proximal end, a distal end, at least one lumen, and at least one port. An exchange port is arranged on at least a distal portion of the catheter body and the exchange port includes at least one lumen configured to receive a guidewire and the catheter body is configured to track over the guidewire to a treatment site. A reentry cannula is slidably arranged with the lumen of the catheter body and is configured to deploy through the catheter body port created upon separation of at least one portion of the distal portion of the elongated catheter. In one embodiment, the reentry cannula is configured to deploy from a first location within the interstitial space of an artery to a second location within a true lumen of the artery upon application of a push or pull control force at a proximal portion the reentry cannula.

Still yet another aspect of the invention is directed towards a reentry catheter for use in forming a pathway in an interstitial space of an artery. The reentry catheter includes a catheter body having a proximal end, a distal end, at least one lumen, and at least one port. An exchange port is arranged on at least a distal portion of the catheter body. The exchange port is configured to receive a guidewire and the catheter body is configured to track over the guidewire to a treatment site. A reentry cannula having a proximal end, a distal end, at least one lumen is configured to be slidably positioned within the lumen of the catheter body. The reentry catheter includes a distal portion configured to slidably separate along the catheter longitudinal axis to provide lateral and axial stability and control to counteract forces realized upon penetration of the reentry cannula through the subintimal vessel layers. Further, the separation of the distal portion of catheter creates an at least one port. The reentry cannula is configured to deploy through the at least one port from a first location within the interstitial space of an artery to a second location within a true lumen of the artery upon application of a force to the tether.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments, of the invention and together with the description serve to explain the principles of the invention.

In the drawings:

FIG. 1 illustrates an exemplary side view of a reentry catheter according to an embodiment of the invention;

FIG. 2 illustrates an exemplary perspective view of the reentry catheter shown in FIG. 1;

FIG. 3 illustrates an exemplary internal view of the reentry catheter shown in FIG. 1;

FIG. 11 illustrates a partially deconstructed side-view of the reentry catheter shown in FIG. 1;

FIG. 12 illustrates a close-up view of a distal portion of the reentry catheter shown in FIG. 11;

FIG. 15A illustrates an exemplary perspective view of a reentry catheter according another embodiment of the invention;

FIG. 15B illustrates an exemplary side-view of the reentry catheter shown in FIG. 15A;

FIG. 16A illustrates an exemplary side view of a reentry catheter in a first configuration according to an embodiment of the invention;

FIG. 16B illustrates an exemplary side view of the reentry catheter in FIG. 16A in a second configuration;

FIG. 16C illustrates an exemplary side view of the reentry catheter in FIG. 16A in a third configuration;

FIG. 16D illustrates an exploded view of components of the reentry catheter in FIG. 16A;

FIG. 17D illustrates an end view of a cannula used in the reentry catheter illustrated in FIG. 17A;

FIG. 17E illustrates an exemplary side view of the reentry catheter illustrated in FIG. 17A in a deployed position;

FIG. 17F illustrates a side view of the reentry catheter according to another embodiment of the invention;

FIG. 17G illustrates a cutting head of the reentry catheter in FIG. 17F;

FIG. 23A illustrates a top view of a marker band in accordance with another embodiment of the invention;

FIG. 23B illustrates the marker band of FIG. 22A on a reentry catheter in a first orientation;

FIG. 23C illustrates the marker band of FIG. 22A on a reentry catheter in a second orientation;

FIG. 23D illustrates the marker band of FIG. 22A on a reentry catheter in a third orientation;

FIG. 23F illustrates a catheter with the marker band shown in FIG. 23A on a reentry catheter in various orientations from 60 left anterior oblique (LAO) to 60 right anterior oblique (RAO);

FIG. 24A illustrates a top view of a marker band in accordance with another embodiment of the invention;

FIG. 24B illustrates the marker band of FIG. 24A on a reentry catheter in a second orientation;

FIG. 24C illustrates the marker band of FIG. 24A on a reentry catheter in a second orientation;

FIG. 24D illustrates the marker band of FIG. 24A on a reentry catheter in a third orientation.

FIG. 25A illustrates a top view of a marker band in accordance with another embodiment of the invention;

FIG. 25B illustrates the marker band of FIG. 25A on a reentry catheter in a first orientation;

FIG. 25C illustrates the marker band of FIG. 25A on a reentry catheter in a second orientation;

FIG. 25D illustrates the marker band of FIG. 25A on a reentry catheter in a third orientation.

FIG. 25E illustrates a catheter with the marker band shown in FIG. 25A in various orientations from 60 left anterior oblique (LAO) to 60 right anterior oblique (RAO);

FIG. 27 illustrates a device manufactured as described in Example 1; and

DETAILED DESCRIPTION OF THE ILLUSTRATED EMBODIMENTS

Figure 4:
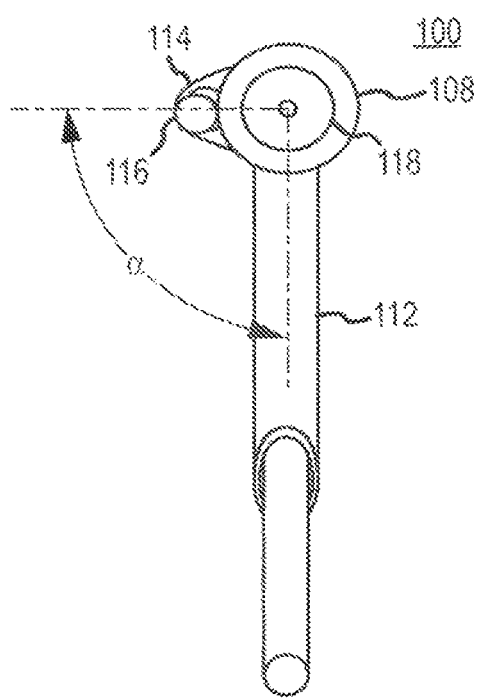
FIG. 4 illustrates an exemplary end view of the reentry catheter shown in FIG. 1.

The invention generally relates to a method and system for crossing an obstruction, e.g., a chronic total occlusion in a blood vessel, and more particularly to a medical device method for crossing an occlusion in a subintimal or interstitial space of an artery. Subintimal or interstitial region or space is at a location beneath at least a portion of intima and preferably at a location contained between the intima and the adventitia of the vessel. The terms tubular member, artery, vessel and bodily passable are used interchangeably throughout the specification.

An embodiment of the invention is directed towards a rapid exchange catheter for insertion into a subintimal space. The catheter includes a proximal end, a distal end, lateral port, and a first lumen configured to receive a first wire. The first lumen extends longitudinally through at least the lateral port of the catheter. The catheter also includes a second lumen having a portion extending distally of the lateral port and also extending through at least the distal end of the catheter. Preferably, the first and second lumens are discontinuous with each other. The catheter further includes an exchange port, e.g., an RX port, arranged along an exterior portion of the catheter body and configured to receive a second wire. The RX port permits the second wire to extend through the RX port and through the second lumen out the distal end of the catheter. The catheter is configured to advance with the second wire via the RX port. This is not an over the wire advancement as known to physicians skilled in the art, but rather utilizes the RX port which permits rapid transfer and aids in orientation of the catheter as described herein.

Another embodiment of invention is directed towards a catheter for insertion into a subintimal space. The catheter includes a proximal end, a distal end, at least one port, and at least one lumen. The at least one lumen extends longitudinally through a port of the catheter. The catheter may also include an exchange port, e.g., RX port, arranged along an exterior portion of the catheter body and configured to receive a second wire or guide wire. The exchange port may be broken into two or more segments along the length of the catheter.

Yet another embodiment is directed towards a reentry catheter for use in forming a pathway in an interstitial space of an artery. The reentry catheter includes a catheter body having a proximal end, a distal end, at least one lumen, and at least one lateral port. A rotating reentry cutter is arranged within the distal end portion of the catheter body and includes a leading edge and pivot attachment points coupled with the catheter body. In one embodiment, at least a portion of the rotating reentry cutter leading edge is configured with one or more sharp surfaces. Alternatively, the cutting surface may extend along the entire surface of the leading edge of the rotating reentry cutter. Preferably, the cutting surface is configured to gain access from the subintimal or interstitial region or space to the true lumen of the vessel. The leading edge of the rotating reentry cutter is configured to deploy through the at least one lateral port from a first location within the interstitial space of an artery to a second location within a true lumen of the artery upon application of a substantially eccentric force to a portion of the rotating reentry cutter. At least one actuator, such a as tendon, tether, coil, cable, linkage of other suitable mechanism is coupled to a portion of the rotating reentry cutter configured to provide the application of a substantially eccentric force in relation to the pivot point. A control handle may be incorporated near the proximal end of the reentry cutter for application of the eccentric force and/or for controlled displacement of the rotating cutter mechanism across the subintimal vessel layers.

Still another embodiment of invention is directed towards a catheter for insertion into a subintimal space. The catheter includes a proximal end, a distal end, and at least one lumen for receiving a guide wire, and a distal portion of the catheter configured to split longitudinally to provide lateral and axial support. At least one port is exposed upon separation of the split catheter distal tip. At least one lumen extends longitudinally through the at least one port of the catheter. The catheter includes a reentry member, e.g., a cannula, which is configured to gain access to a vessel true lumen from a subintimal space. The cannula is configured to penetrate the vessel layers adjacent to the at least one port. The cannula is configured to have a hollow portion to receive an interventional guide wire. The at least one lumen extends longitudinally through at least the port of the catheter.

Another embodiment is directed towards a reentry catheter for use in forming a pathway in an interstitial space of an artery. The reentry catheter includes a catheter body having a proximal end, a distal end, at least one lumen, and at least one port. An exchange port is arranged on at least a distal portion of the catheter body. The exchange port includes at least one lumen configured to receive a guidewire and the catheter body is configured to track over the guidewire to a treatment site. The reentry cannula includes a proximal end, a distal end, at least one lumen extending from the proximal end to the distal end. A tendon is coupled to a distal end portion of the reentry catheter. The tendon is configured to unlock the distal portion mechanism and the linear extension of the reentry cannula. The tendon can also be used to aid in the retraction of the split catheter distal portion from an extended to closed configuration.

In another embodiment, the reentry cannula includes a lumen for receiving a guide wire or supplemental treatment device. The supplemental treatment device may include guide wires, medical instruments, balloons, stents, laser catheters, optical fibers, visualization devices, medications and other medical instruments known in the art. In a preferred embodiment, the lumen portion of the reentry member is configured to receive a guide wire having a diameter in a range from about 0.01 inches to about 0.04 inches or larger.

In yet another embodiment, a catheter system includes a catheter body having a proximal end, a distal end, a split distal portion, and at least one lumen wherein the lumen includes an opening. The split distal portion is configured to separate upon actuation of a pull or push mechanism to expose the at least one port, to provide a space for extension of the reentry cannula, and to allow the reentry cannula to reenter the true vessel lumen from the subintimal space. The split distal portion is configured to slide linearly while preventing radial expansion or separation.

In another embodiment, the reentry cannula is moveable, flexible and/or bendable from a first configuration to a second configuration, e.g., a retracted position to an operative position. The movement may be achieved upon application of a force, e.g., an axial push force or pull force applied to a portion of the reentry cannula. In some embodiments, the force may be generated with at least one of a push member; ramp; wedge; and electrically activated materials, including electroactive polymers, thermo-active polymers, electroactive metals and combinations thereof.

Moreover, these electrically activated materials may be activated with an electrical signal such as current or voltage as known in the art. For example, the catheter body or the reentry member may be constructed as described in U.S. Pat. No. 7,951,186, which is hereby incorporated by reference.

In other embodiments, at least a portion of the reentry cannula may have a load or force built into the member. For example, the reentry cannula may have pre-resilient shape contained within the rigid distal portion of the catheter or other structure that prevents movement. After the split distal portion separates or other structure is removed, the reentry cannula is released from a first position to second position.

Optionally, any catheter herein may include an exchange port, e.g., RX port, arranged along an exterior portion of the catheter body and configured to receive a second wire or guide wire. The exchange port may be broken into two or more segments along the length of the catheter.

In a preferred embodiment, the first wire and second wire are guidewires, which may have diameters in a range from about 0.01 inches to about 0.04 inches or larger. The diameter of the first and second wire may be different. The lateral port is oriented in range from about 0 degrees to about 180 degrees relative to the exchange port, preferably at about 25 degrees to about 90 degrees relative to the exchange port, and more preferably between about 40 degrees and about 75 degrees relative to the exchange port.

The catheter may be constructed from various materials as known in the art. For example, the catheter may be constructed from materials such as polyesters; polyurethanes; polyamides; polyolefins including polyethylene and polypropylene; and any copolymers thereof. Some more specific examples of suitable materials include, but are not limited to: nylon; polyester elastomer; polyether/block polyamide, such as PEBAX, Hytrel, and/or Arnitel; polyamid such as Grilamid; fluoro-polymer, such as Kynar; polyether other ketone (PEEK); polyethylene (PE); polyurethane; polyolefin copolymer (POC); and tetrafluoroethylenes, such as polytetrafluoroethylene (PTFE).

Other suitable materials for the catheter include steel, including laser cut stainless steel. The catheter may comprise coils as described in U.S. Publication No. 2010/0063534, which is hereby incorporated by reference as if fully set forth herein.

The cannula can be constructed of various materials, e.g., steel, alloy, nitinol, combinations thereof and the like. The cannula is configured to permit other devices to be operated through the lumen of the cannula, e.g., a balloon, cutting device, guidewire, and the like. In addition, the cannula may be configured to have a predetermined shape, i.e., resilient shape, straight shape, curved shaped, memory shape. In a preferred embodiment, the cannula may also be sized to accommodate a wide range of guidewire diameters ranging from about 0.01 inches to about 0.04 inches or larger.

Suitable materials for the split distal portion include rigid materials including but not limited to stainless steel, reinforced polymers, titanium, alloys, other metals or rigid materials coated with a biocompatible coating, and combinations thereof and the like.

Another embodiment of the invention is directed towards a method for crossing an obstruction in blood vessel. The method includes advancing a first wire into an interstitial space of a vessel. In some instances with severe calcification present, an undersized low profile balloon or other intervention dilation device may be used to pre-dilate the subintimal space prior to introduction of the rapid exchange catheter. Next, a rapid exchanger catheter is advanced into the subintimal space with the first wire. That is, the rapid exchange catheter is advanced along the first wire with the aid of the exchange port. A second wire is advanced down a central lumen of the rapid exchange catheter and the second wire is advanced through a lateral port of the rapid exchange catheter system into the lumen of the blood vessel. Preferably, a cannula is configured to exit the lateral port into the true lumen of the vessel from the subintimal space prior to the second wire being advanced through the lateral port. However, a cannula need not be utilized.

Another embodiment of the invention is directed towards a method for crossing an obstruction in a blood vessel. The method includes advancing a first guide wire through a true lumen of vessel and into an interstitial space of the vessel. In some instances with severe calcification present, and undersized low profile balloon or other intervention dilation device may be used to pre-dilate the subintimal space prior to introduction of the reentry catheter. Next, the reentry catheter is advanced into the subintimal space through either an over the wire or via a rapid exchange technique with the reentry member in a stowed position. The catheter then advances through the subintimal space until the lateral port is distal to the total occlusion.

The orientation and the location of the catheter and its lateral port with respect to the occlusion may be directed through the use of radiopaque markers and visualization techniques known in the art. Once the catheter has been properly oriented, the operator moves the reentry cannula or the split distal catheter portion from the stowed or locked position and subsequently separates the bottom and top layers of the split distal portion such that a cantilevered distal extension is in position to provide lateral and axial stability upon reentry. The reentry cannula is then advanced adjacent the at least one port and advanced for a precise penetration between the subintimal space and the true vessel lumen. A second interventional guide wire, in the case of a rapid exchange catheter, or the first guide wire for an over the wire configuration is advanced into the vessel lumen through the hollow portion of the reentry member. Once the intervention wire is in place, the reentry member may be retracted and the reentry cannula is retracted, the split catheter distal portion is retracted and locked, and the entire reentry catheter removed. Of course, more than one wire may also be used in the over the wire technique.

Yet another embodiment of the invention is directed towards a kit. The kit includes a catheter according to embodiments of the invention and directions for use. The kit may also include a supplemental treatment device, e.g., a balloon, optical catheter, visualization catheter, stent, embolic protection device and the like. In addition, the kit may include valves and other devices that may be used in medical procedures.

Reference will now be made in detail to an embodiment of the present invention, example of which is illustrated in the accompanying drawings.

FIG. 1 illustrates a side view of a reentry catheter according to an embodiment of the invention. FIG. 2 illustrates a perspective view of the reentry catheter shown in FIG. 1. FIG. 3 illustrates an internal view of the reentry catheter shown in FIG. 1.

Referring to FIGS. 1-3, a reentry catheter according to this embodiment is generally depicted as reference number 100. The catheter 100 is configured to permit a user to cross an obstruction, e.g., partial or total occlusion, in a subintimal space of a vessel. The catheter 100 also enables fast and simple true lumen reentry without the need for visualization, e.g., IMUS visualization. The visualization may be active or passive as known in the art or described with reference towards U.S. Patent Application Publication No. 2005/0171478, which is hereby incorporated by reference.

The catheter 100 is flexible and has a proximal end 102 and a distal end 104. The proximal end 102 is attached to a handle (not shown). A shaft 106 extends from the proximal end 102 of the catheter to the distal end of a rigid shroud 108. A lateral port 110 is located near the distal end and preferably in the rigid shroud 108. Alternatively, or in addition to, a lateral port (not shown) may also be located in the shaft 106 and/or molded end portion 118. The shaft 106 includes a central lumen (not shown) extending at least partially along the entire shaft 106. A flexible cannula 112 may be contained in the inner lumen of the shaft 106 along substantially the length of the catheter 100. The distal end of the shaft 106 is connected to the proximal end of the shroud 108, preferably by a laser weld, glue, over-molding or the like as known in the art. There may be more than one lateral port at a distal portion of the shroud 108. As discussed below, the shroud 108 includes a molded end portion 118, and the shroud 108 includes a guidewire lumen beginning at the proximal end of the wire guide 120, wherein the proximal end of the wire guide has a proximal port 113 adjacent thereto, and the guidewire lumen ends at a distal port 115 in the rigid shroud 108, wherein the distal port 115 is disposed distally of the proximal port 113. As illustrated in FIGS. 1-3, the exchange port 114 is disposed proximally of the lateral port 110, and the proximal port 113 is disposed distally of the lateral port 110.

The cannula 112 can be configured to permit other devices or supplemental devices to be operated through the lumen of the cannula 112, e.g., balloon, cutting device, guidewire, filters, optical devices, e.g., RF or laser ablation devices, and the like. In addition, the cannula 112 may be configured to have a predetermined shape, i.e., resilient shape, straight shape, curved shaped, memory shape. In a preferred embodiment, the cannula 112 may also be sized to accommodate a wide range of guidewire diameters ranging from about 0.01 inches to about 0.04 inches or larger. Moreover, a second guidewire 121 having the foregoing dimensions is configured to exit a lumen of the cannula 112 in a preferred embodiment.

In a preferred embodiment, an exchange port 114, e.g., a rapid exchange port, is eccentrically located near the distal end of the shaft 106. The port 114 includes a jacketed polyimide tube trimmed flush to the profile of the device after processing to facilitate tracking and back loading of a guidewire 116. Preferably, the guidewire 116 can have a diameter in a range from about 0.01 inches to about 0.04 inches or greater and be constructed of a range of materials as known in the art. In addition, the wire 116 may have lubricous coating, e.g., PVP thin film or PTFE, and/or a predetermined shape.

Optionally, a moulded end portion 118 is coupled to the distal end of the shroud 108. The molded end portion 118 is configured to provide improved lateral support for launching the cannula 112 from a subintimal space to a vessel true lumen. For example, the molded end portion 118 provides an optional lateral extension, which is configured to provide stability during the initial orientation of the device over the central arc of the lesion. Referring to FIG. 2, the molded end portion 118 is configured to contain a wire guide 120. The wire guide 120 is configured to deliver a guidewire 116 from the exchange port 114 to the molded end portion 118. In this embodiment, the guidewire 116 exits the distal end of the rapid exchange port 114, enters the proximal end of the wire guide 120 and exits through a lumen near the distal end 104 of the molded end portion 118. In this embodiment, the wire lumens are interrupted to maintain compatibility with smaller profile crossover sheaths. The use of a discontinuous wire guide allows the outer diameter of the device to be smaller than would otherwise be required if a wire guide tube (not shown) were to travel parallel to the shaft center lumen along the rapid exchange port 114, along the shroud 108, and along the molded end portion 118. Another embodiment of the invention utilizes a non-discontinuous wire guide. Moreover, the alignment of the exchange port 114 and the wire guide 10 allow for back loading of the exchange wire 116.

Figure 5:
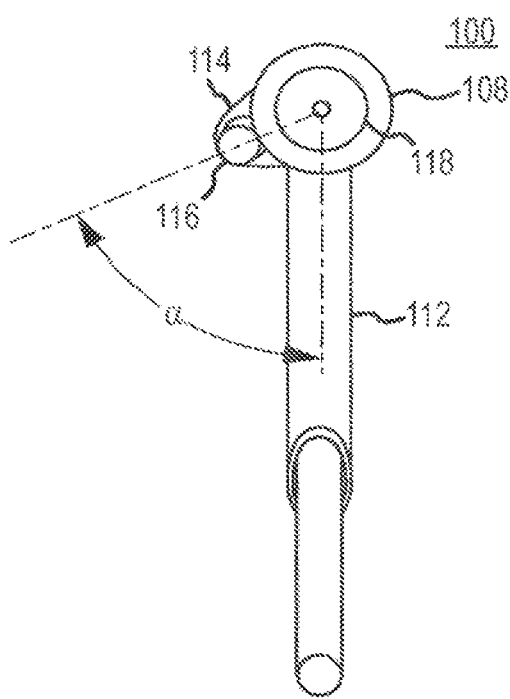
FIG. 5 illustrates an exemplary end view of a reentry catheter according to another embodiment of the invention.
Figure 6:
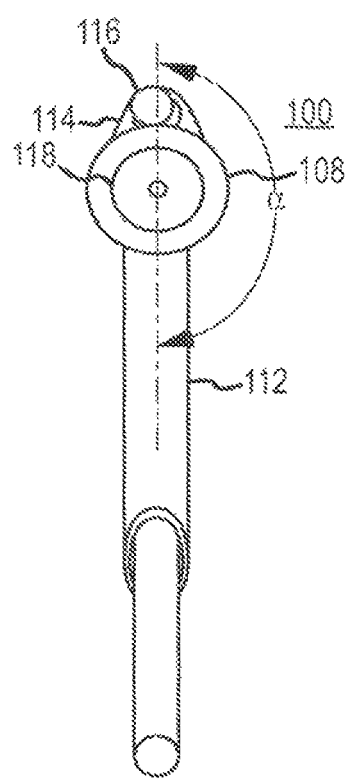
FIG. 6 illustrates an exemplary end view of a reentry catheter according to another embodiment of the invention.

FIG. 4 illustrates an exemplary end view of the reentry catheter shown in FIG. 1. FIG. 5 illustrates an exemplary end view of a reentry catheter according to another embodiment of the invention. FIG. 6 illustrates an exemplary end view of a reentry catheter according to another embodiment of the invention.

Referring to FIGS. 4-6, an angle α is defined between the axis of the rapid exchange port 114 and the central lumen axis of the lateral port 110. More specifically, FIG. 4 shows a reentry catheter 100 where the angle α is at about a 90 degree orientation between the axis of the lateral port 110 and a central lumen axis of the rapid exchange port 114. FIG. 5 illustrates a reentry catheter 100 where angel α is at about a 65 degree orientation between the axis of the lateral port 110 and a central lumen axis of the exchange port 114. FIG. 6 shows a reentry catheter 100 where angle α includes about a 180 degree orientation between the axis of the lateral port 110 and a central lumen axis of the rapid exchange port 114.

In this embodiment, the cannula 112 would exit out the central lumen of the catheter and the rigid shroud 108. In a preferred embodiment as depicted in FIG. 5, the catheter is optimally sized for use in a 4 mm vessel where the natural tendency of the catheter will be to align along the outer surface of the vessel layer with the cannula in the launched position either oriented radially toward the central axis of the true vessel lumen or radially outward in a direction approximately 180 degrees away from the true vessel lumen central axis. While the angle α may be optimally sized for a particular vessel size, e.g., a 4 mm vessel, operation of the device is not restricted to a specific vessel size. Moreover, angle α may be in a range from about 0 degrees to about 360 degrees, preferably angle α is in a range from about 25 degrees to about 90 degrees, and more preferably angle α is in a range from about 40 degrees to about 75 degrees.

Figure 7:
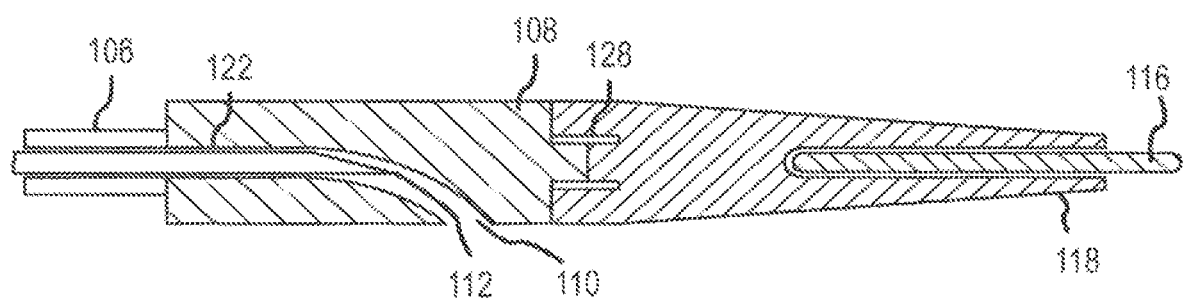
FIG. 7 illustrates a close-up partial cross-sectional view of a distal portion of the reentry catheter shown in FIG. 1 with a cannula in a retracted position.
Figure 8:
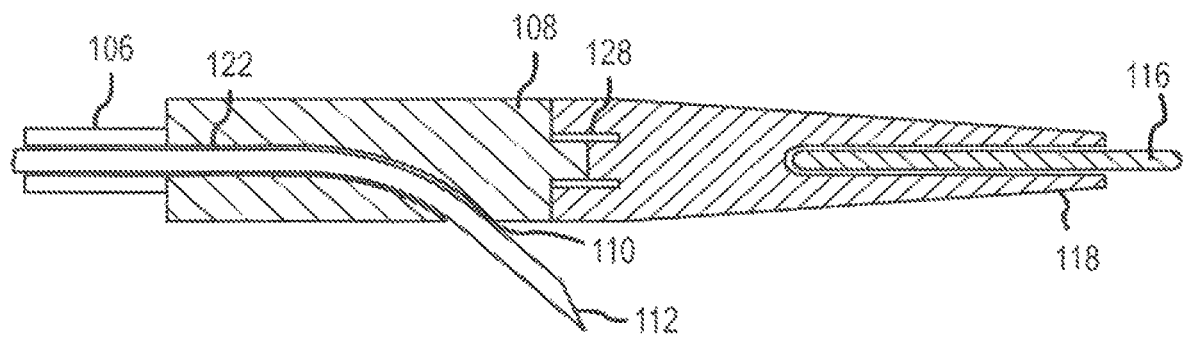
FIG. 8 illustrates a close-up partial cross-sectional view of a distal portion the reentry catheter shown in FIG. 1 with a cannula in an advanced position.
Figure 9:
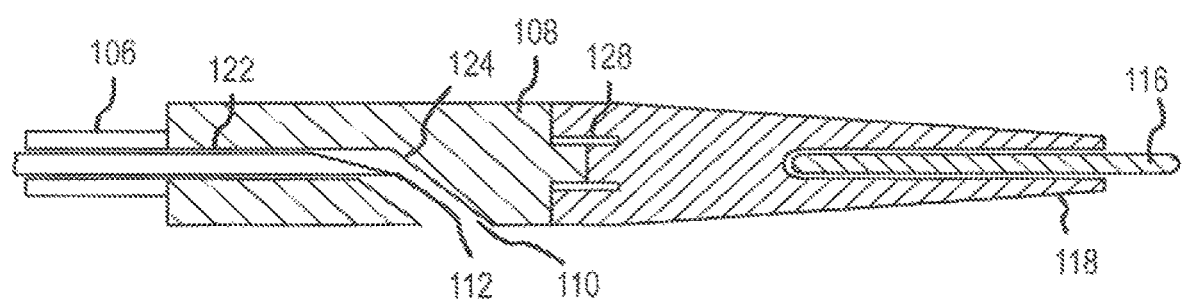
FIG. 9 illustrates a close-up cross-sectional view of a distal portion of the reentry catheter according to FIG. 1 with a cannula in a retracted position.
Figure 10:
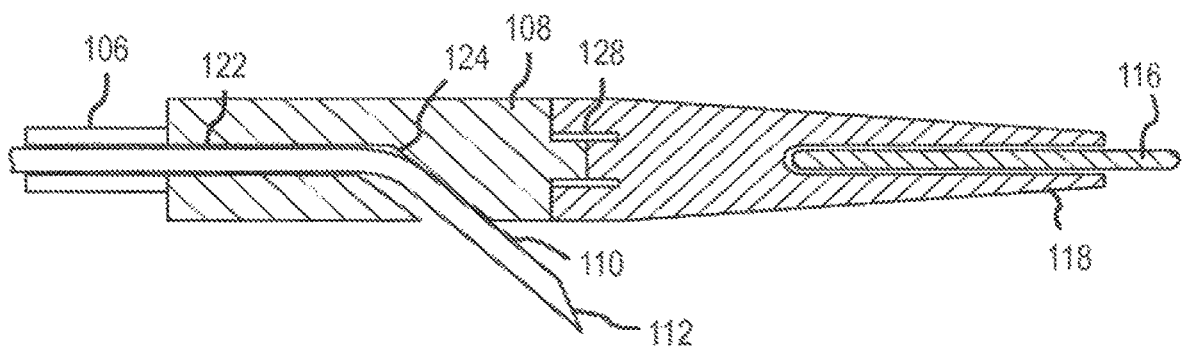
FIG. 10 illustrates a close-up cross-sectional view of a distal portion of the reentry catheter shown in FIG. 9 with a cannula in an advanced position.

FIG. 7 illustrates a close-up partial cross-sectional view of a distal portion the reentry catheter shown in FIG. 1 with a cannula in a retracted position. FIG. 8 illustrates a close-up partial cross-sectional view of a distal portion of the reentry catheter shown in FIG. 1 with a cannula in an advanced position. FIG. 9 illustrates a close-up cross-sectional view of a distal portion of the reentry catheter according to FIG. 1 with a cannula in a retracted position. FIG. 10 illustrates a close-up cross-sectional view of a distal portion of the reentry catheter shown in FIG. 9 with a cannula in an advanced position.

Referring to FIGS. 7-10, different configurations can be used to deflect the cannula 112 or wire 116 towards the true lumen of the vessel from an interluminal location. In FIGS. 7-8, the catheter 100 includes an internal shaped tube 122 within the rigid shroud 108 near the lateral port 110. The cannula 112 is configured to exit through the lateral port 110 along an arc formed by the internal shaped tube 122. The arc upon exit from the lateral port may range from about 5 degrees to about 95 degrees measured from the central longitudinal axis of the catheter. In a preferred embodiment, the internal shaped tube 122 includes an arc shaped end region upon exit from the lateral port ranges from about 5 degrees to about 85 degrees and preferably about 20 degrees to about 45 degrees. In this embodiment, the internal shaped tube 12 is contained within the rigid shroud 108 and is not integrated directly into the molded end portion 118 or shaft 106. However, the internal shaped tube may be integrated directly into the molded end portion 118 or shaft 106 and the lateral port may exit at that location.

Referring now to FIGS. 9 and 10, a deflection ramp is utilized to guide the cannula 112 or wire 116 towards the inner lumen of a vessel. The catheter in this embodiment includes a deflection ramp 124 near the lateral port 110. The deflection ramp 124 is positioned in the shroud 108. The flexible cannula 112 is configured to be deflected by the ramp 124 and exit the lateral port 110. The angle of the ramp 124 can range from about 5 degrees to about 85 degrees and preferably from about 20 degrees to about 45 degrees with respect to the central lumen axis of the shaft 106. This preferred angle of exit for the cannula through the lateral port and into the true vessel lumen provides a clear advantage. A more orthogonal approach relies on the hoop strength of the vessel to support reentry forces. During penetration with a more orthogonal angle of approach, the vessel wall may tend to pull away from the cannula tip such that penetration will require an increased force application and possible multiple attempts to successfully enter the true vessel lumen. Also, it is thought that by reentering the true vessel lumen at a lower approach angle, the vessel wall penetration is supported by the longitudinal strength of the vessel wall and less reentry force is required, thereby creating a lateral dissection plane through the vessel wall. Therefore, a lower approach angle results in less resistance to penetration. This feature coupled with the improved torsional strength of the shaft, as described below, results in more consistent reentry at a preferred location closer to the distal end of the occlusion.

FIG. 11 illustrates a partially deconstructed side-view of the reentry catheter shown in FIG. 1. FIG. 12 illustrates a close-up view of a distal portion of the reentry catheter shown in FIG. 11.

Referring to FIGS. 11-12, the catheter 100 includes a shaft 106 that can be constructed of materials as discussed therein. In this embodiment the shaft 106 includes a triplex coil construction also referred to as a drive cable or torque tube. This triplex coil includes an outer jacket 150 and three coils each would in opposite directions and then fixed at the ends by welding. The three coils include a first coil 152, a second coil 154, and a third coil 156. In this embodiment, the distal end of the coil jacket 150 is attached to the proximal end of the rigid shroud 108 by a laser weld or other attachment procedure as known in the art. Referring to FIG. 12, the cannula 112 is contained in an inner lumen defined by the coils. This coil design provides enhanced flexibility for navigating tortuous vasculature while delivering superior torque transmission and torque control properties compared to a braided or double braided shaft. As an example, the coils can be constructed of stainless steel flat wire, alloy wire, or other metal. Of course, the shaft may also be constructed of other conventional materials, i.e., braided, double braided, and the like as known in the art. In a preferred embodiment, the windings of the coils are orientated oppositely with respect to each adjacent coil. An optional molded end portion 118 is configured to provide improved lateral support for launch of cannula 112 from a subintimal space to a vessel true lumen.

Figure 13:
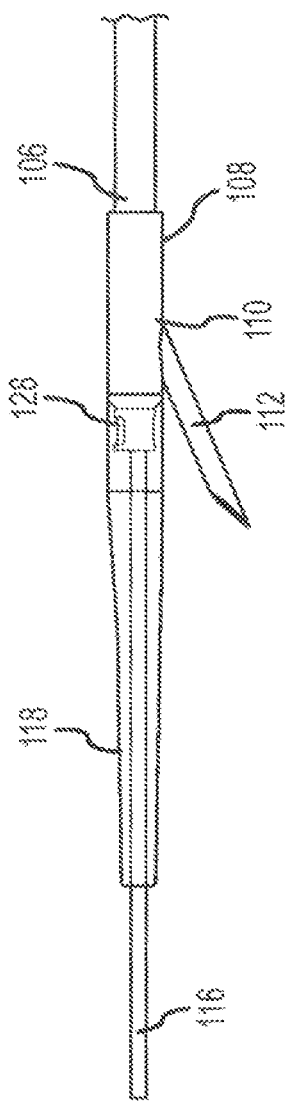
FIG. 13 illustrates a close-up view of a distal portion of the reentry catheter shown in FIG. 1.
Figure 14A:
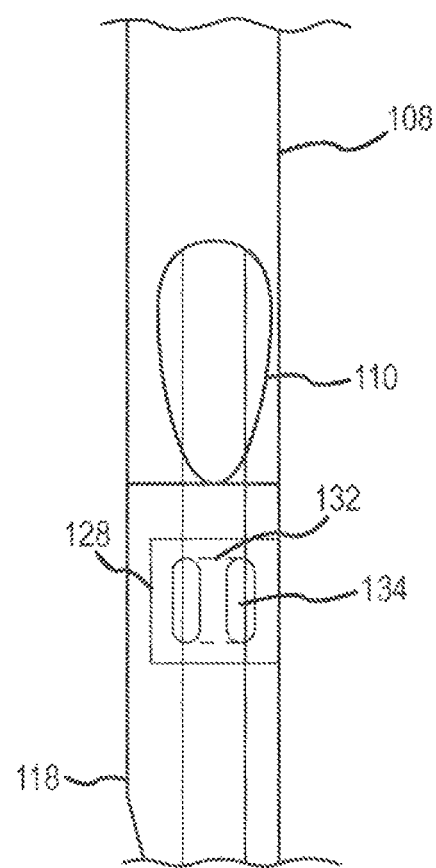
FIG. 14A illustrates a close-up view of a distal portion of the reentry catheter shown in FIG. 1.

FIG. 13 illustrates a close-up view of a distal portion of the reentry catheter shown in FIG. 1. FIG. 14A illustrates a close-up view of a distal portion of the reentry catheter shown in FIG. 1.

Referring to FIGS. 13 and 14A, the catheter 100 optionally may include at least one orientation marker 128 or a plurality of orientation markers (not shown). In a preferred embodiment, the orientation markers 128 are configured to ensure orientation of the lateral port towards the true lumen of the vessel. The orientation markers 128 may also be configured to determine a spatial relationship of other attributes of the catheter, e.g., the spatial location of the distal end of the catheter 104. In a preferred embodiment, the marker 128 is arranged near a distal portion of the catheter 100. The marker 128 is configured as a radiopaque band around a distal portion of the rigid shroud 108 at a proximal portion of the molded tip 118. The over molded tip 118 would then be secured over the marker band.

Figure 18A:
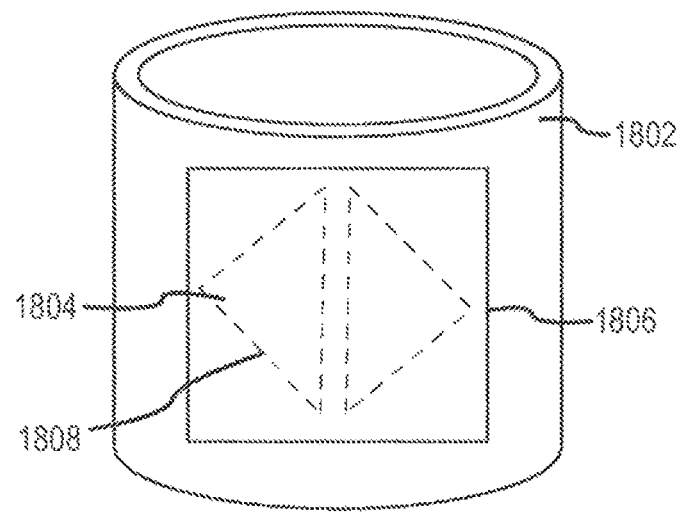
FIG. 18A illustrates a marker band in accordance with another embodiment of the invention.
Figure 18B:
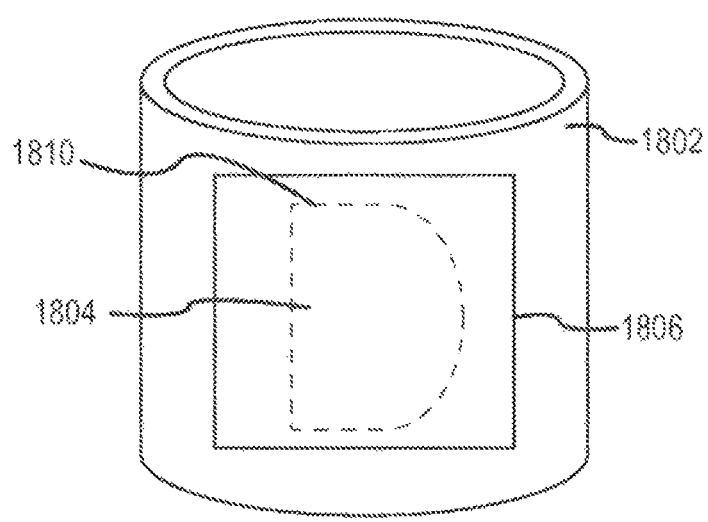
FIG. 18B illustrates a marker band in accordance with another embodiment of the invention.

The marker 128 may be in the form of a marker band as described herein and epoxied, welded, soldered or press fit over the distal end of the rigid shroud 108. The flexible molded tip 118 then fits over the marker band 118. In one embodiment as shown in FIGS. 18A-18B, cut outs or windows 1806 on the marker band are configured such that different views on fluoroscopic images enable the operator to align the lateral port 110 so that the cannula 112 or other instrument, e.g., guidewire, working element, and the like, could be aligned such that deployment directs the cannula toward the true lumen of the vessel rather than in a direction away from the true lumen of the vessel.

Referring to FIG. 14A, the catheter 100 includes at least one orientation marker 128 or a plurality of orientation markers (not shown). In a preferred embodiment, the orientation markers are configured to ensure orientation of the lateral port towards the true lumen of the vessel. The orientation markers may also be configured to determine a spatial relationship of other attributes of the catheter, e.g., the spatial location of the distal end of the catheter. In a preferred embodiment, the marker 128 is arranged near a distal portion of the catheter. The marker 128 is configured as a radiopaque band around a distal portion of the rigid shroud 108 at a proximal portion of the molded tip 118. The over molded tip 118 would then be secured over the marker band. The marker band 128 in this embodiment includes a second pattern cut out 132 in the form of two longitudinal slots 134 as described herein with reference to FIGS. 18A-25F.

FIG. 15A illustrates an exemplary perspective view of the reentry catheter according to another embodiment of the invention. FIG. 15B illustrates an exemplary side-view of the reentry catheter shown in FIG. 15A.

Referring to FIGS. 15A-15B, a reentry catheter according to this embodiment is generally depicted as reference number 200. The catheter 200 is configured to permit a user to cross an occlusion in a subintimal space of a vessel. The catheter 200 is similar to the catheter described with reference to FIGS. 1-3. That is, the catheter 200 enables fast and simple true lumen reentry without the need for active guided visualization, e.g., IVUS visualization, at a location near the physician's preferred location distal the total occlusion. The catheter 200 is flexible and has a proximal end 202 and a distal end 204. The proximal end 202 is attached to a handle (not shown).

A shaft 206 extends from the proximal end 202 of the catheter to the distal end of a rigid shroud 208. A lateral port 210 is located near the distal end and preferably in the rigid shroud 208. The shaft 206 includes a central lumen (not shown) extending at least partially along the entire shaft 206. A flexible cannula 212 may be contained in the inner lumen of the shaft 206 along substantially the length of the catheter 200. The distal end of the shaft 206 is connected to the proximal end of the shroud 208 preferably by a laser weld, glue, or the like as known in the art. There may be more than one lateral port configured within the shroud 208 or before the shroud 208.

The cannula 212 can be configured to permit other devices to be operated through the lumen of the cannula 212, e.g., a balloon, cutting device, guidewire, and the like. In addition, the cannula 212 may be configured to have a predetermined shape, i.e., resilient shape, straight shape, curved shaped, memory shape. In a preferred embodiment, the cannula 212 may also be sized to accommodate a guidewire 215. The guidewire 215 may have a diameter in a range from about 0.01 inches to about 0.04 inches or larger. In some embodiments the cannula 212 can have a lumen sized to support the delivery of vascular treatments through the subintimal space into the vessel true lumen without the assistance of a separate cannula or treatment guidewire.

In a preferred embodiment, a port 214, e.g., a rapid exchange port is eccentrically located near the distal end of the shaft 206. The port 214 includes a jacketed polyimide tube trimmed flush to the profile of the device after processing to facilitate tracking and back loading of a wire 216, e.g., an exchange wire. The wire 216, e.g., an exchange wire, can range in diameter from about 0.01 inches to about 0.04 inches or larger and be constructed of a range of materials as known in the art. In addition, the wire 216 may have lubricous coating, e.g., PVP thin film or PTFE, and/or a predetermined shape. In this embodiment, there is no molded end portion as shown in FIGS. 1-3.

FIG. 16A illustrates an exemplary side view of a reentry catheter in a first configuration according to an embodiment of the invention. FIG. 16B illustrates an exemplary side view of the reentry catheter in FIG. 16A in a second configuration. FIG. 16C illustrates an exemplary side view of the reentry catheter in FIG. 16A in a third configuration.

Referring to FIG. 16A, a reentry catheter according to this embodiment is generally depicted as reference number 1600. The catheter is configured to permit a user to cross an obstruction, e.g., a partial or total occlusion, in a subintimal space of a vessel. The catheter also enables fast and simple true lumen reentry without the need for active visualization, e.g., IVUS visualization. Visualization may be used to assist procedures of the invention, e.g., the visualization may be active or passive. In one embodiment, visualization features are added as described with reference towards U.S. Patent Application Publication No. 2005/0171478, which is hereby incorporated by reference.

The catheter 1600 includes a split tip distal portion 1602 coupled to a shaft coupler 1604 and a catheter shaft 1606 including at least one lumen 1608. The lumen 1608 of the catheter shaft 1606 is configured to receive a reentry cannula 1610 slidably disposed within the at least one lumen 1608. The cannula 1610 can be configured to permit other devices to be operated through the lumen of the cannula 1610, e.g., a balloon, cutting device, guidewire, and the like. In addition, the cannula 1610 may be configured to have a predetermined shape, i.e., resilient shape, straight shape, curved shaped, memory shape. In a preferred embodiment, the cannula 1610 may also be sized to accommodate a wide range of guidewire diameters such as guidewire diameters in a range from about 0.01 inches to about 0.04 inches or larger. In some embodiments the cannula 1610 can have a lumen sized to support the delivery of vascular treatments through the subintimal space into the vessel is true lumen without the assistance of a separate cannula or treatment guidewire.

The reentry cannula 1610 may be configured to permit other devices or supplemental devices to be operated through the lumen of the cannula. The supplemental devices may include a balloon, a cutting device, a thrombectomy device, a guidewire, filters, e.g., an embolic filter, optical devices, RF or laser ablation devices or combinations and the like. In addition, the reentry cannula may be configured to have a predetermined shape, e.g., pre-resilient shape, straight shape, curved shaped, memory shape and combinations of the same.

In a preferred embodiment, the catheter is flexible and has a proximal end and a distal end. The proximal end is attached to a handle (not shown). The shaft 1606 extends from the proximal end of the catheter to the distal end of a shaft coupler 1604 or the split distal portion 1602. The shaft 1606 may be constructed of conventional techniques. In a preferred embodiment, the shaft 1606 includes braided, double braided, or triplex construction as described with reference to FIGS. 11 and 12 herein. The first orientation in FIG. 16A is a closed configuration or the split tip 1602 portion in a home position.

Referring to FIGS. 16B-16C, the catheter 1600 is in a second and third configuration. The second configuration is positioned having the split tip 1602 in an open configuration, e.g., one portion of the split tip extends past another portion of the split tip to expose a port or opening 1612. The extension can either occur as a result of the cannula 1610 pushing an upper split tip-portion 1614 past a bottom split tip portion 1619 or by translation of a push force directly on the split tip top portion.

Alternatively, or additionally, a distal port (not shown) may also be located in the shaft. The shaft 1606 includes at least one lumen extending at least partially along the entire shaft and exiting out of the catheter distal end. In FIG. 16C, the cannula 1610 extends out of a port or opening 1612 of the catheter 1600, e.g., deflects off a ramp on an internal portion of the catheter. A wire 1616, e.g., Kevlar tendon having a high tensile strength and low bend stiffness is configured to retract the upper split 1614 tip from an extended position to a home position. In a preferred embodiment, the tendon 1616 is coupled to an upper spilt 1614 tip at a location 1618.

FIG. 16D illustrates an exploded view of the components of the reentry catheter in FIG. 16A.

Referring to FIG. 16D, the various catheter components are illustrated and included a distal end of shaft 1606 connected to the proximal end of a rigid shaft coupler 1604. In one embodiment, the shaft 1606 is connected to the shaft coupler 1604 by laser welding, glue, over-molding or other techniques as known in the art. The distal end of the coupler 1604 is coupled with the rigid shroud cover 1615 and the split tip bottom portion 1619. The shroud cover 1615 may include stainless steel or other suitable material. The split tip top portion 1614 is slidably coupled with the split tip bottom portion 1619. A lumen 1608 is disposed in the catheter shaft 1606, and can be fabricated of PTFE or other suitable thermoplastic material as known in the art. The lumen may optionally include a liner 1620 made of thermoplastic material, e.g., a PTFE liner. A reentry cannula 1610, made of nitinol or other suitable material as described herein, is disposed within at least one lumen 1608 and extends from the proximal end to the distal portion of the catheter. A tendon 1616, made of Kevlar or other suitable material with a high tensile strength and a low bend stiffness, is coupled to a distal portion of the reentry cannula and fastened to a proximal portion of the split tip top. The tendon 1616 may also be arranged in a lumen 1617, e.g., PTFE braided lumen. A flexible atraumatic tip may be attached to the distal end of the split tip top by laser weld, glue, over-molding or the like.

Figure 16E:
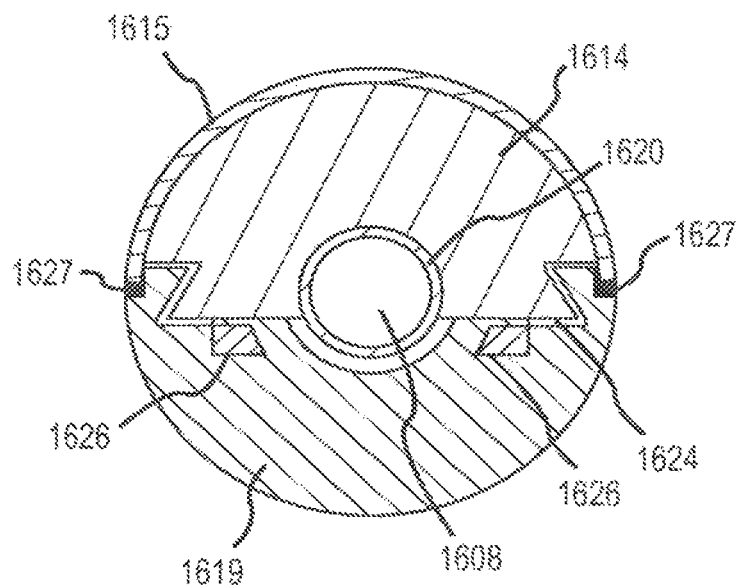
FIG. 16E illustrates a cross-sectional view of the reentry catheter in FIG. 6A along line C to C1.
Figure 16F:
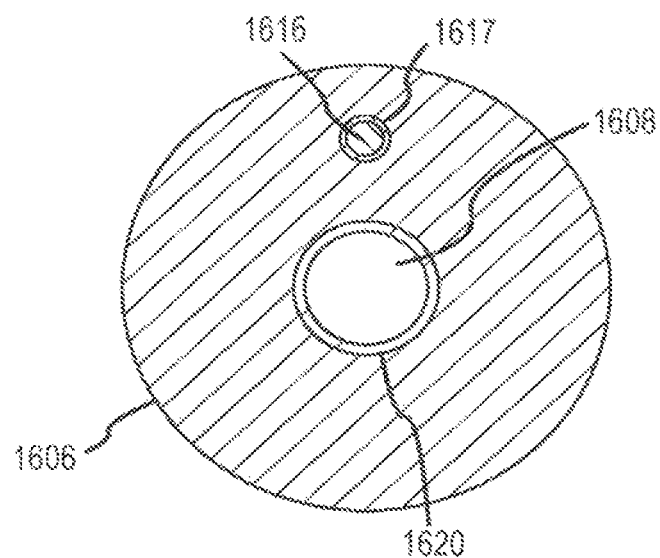
FIG. 16F illustrates a cross-sectional view of the reentry catheter in FIG. 16A along line D to D1.

FIG. 16E illustrates a cross-sectional view of the reentry catheter in FIG. 16A along line C to C1. FIG. 16F illustrates a cross-sectional view of the reentry catheter in FIG. 16A along line D to D1.

Referring to FIG. 16E, the split tip top portion 1614 and split tip bottom portion 1619 are keyed in a dove tail configuration 1624 to provide a slidably locking interface. Hard stops 1626 are incorporated in the split tip to prevent over extension of the split top portion 1614. The shroud cover 1615 is welded at least at weld joints 1627 to the split tip bottom 1619 thereby prohibiting the cannula from exiting through a port 180 degrees opposite the desired reentry direction. While a dovetail configuration is shown, other keyed or locking interfaces can be utilized. Additionally, linear slides or bearing surfaces can also be incorporated. Referring now to FIG. 16F, a cross-section view of the catheter shaft at a location proximal to the shaft coupler is depicted. In this configuration, a lumen 1617 is constructed of a low friction material, such as PTFE, within the catheter shaft. This lumen 1617 contains the tendon 1616 which is used to control the retraction of the split upper tip 1614 from an extended to a stored or home position. In operation, the distal tip portion is docked in a non-extended and locked position and the reentry catheter is docked in a straight position, as shown in FIG. 16A while traversing through an artery and into or reversed out of the subintimal vessel space.

In another embodiment, at least one marker as described herein, e.g., a radiopaque marker, is disposed on the body of the catheter near its distal end or integrated within the body of the catheter. The radiopaque marker is used with standard visualization techniques, e.g., fluoroscopy, to guide the catheter through the body and into position in the subintimal space, to position the port 1612 and rotating reentry cannula 1610 at a desired location distal to the occlusion, and to determine whether the rotating reentry cutter is in the stowed, ready, or in a fully deployed position.

During use of this device, an operator could mechanically control and position the device as similarly described with reference to FIGS. 26A-26F. In this embodiment, a user could open the split tip 1602 when the catheter after the catheter is in the desired position at a location distal to the occlusion. By way of example, an operator could mechanically control the reentry cannula by holding the catheter and advancing the cannula such that the distal end pushes or extends the split tip top 1614 to provide a cantilevered support and opening 1612. In another embodiment, the operator could extend the split tip top 1614 by exertion of a push or other appropriate force applied to the proximal end of the split tip top 1614 with a mechanical rod or other means.

Figure 26A:
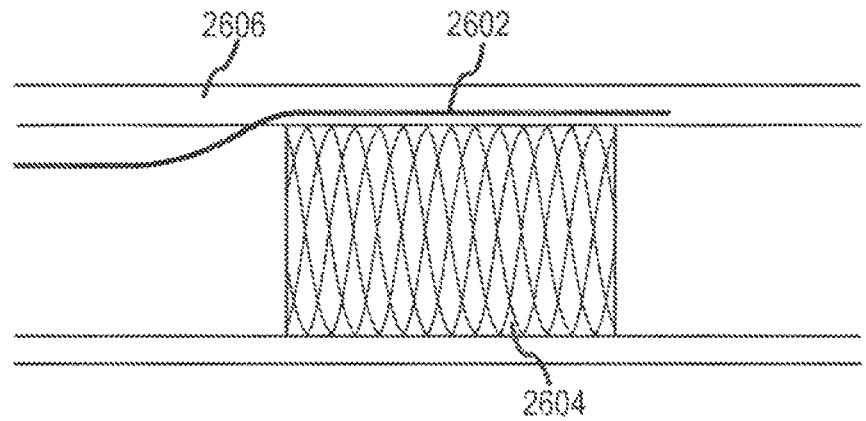
FIGS. 26A-26F illustrates an exemplary method for using a medical device of FIG. 1.
Figure 26B:
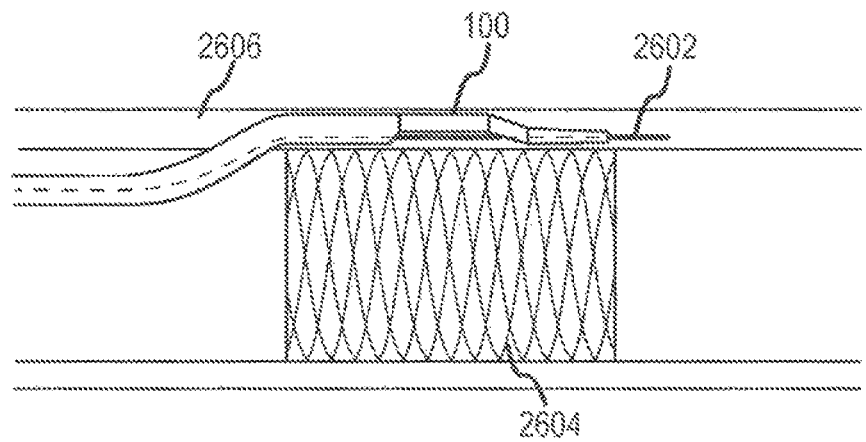
Figure 26C:
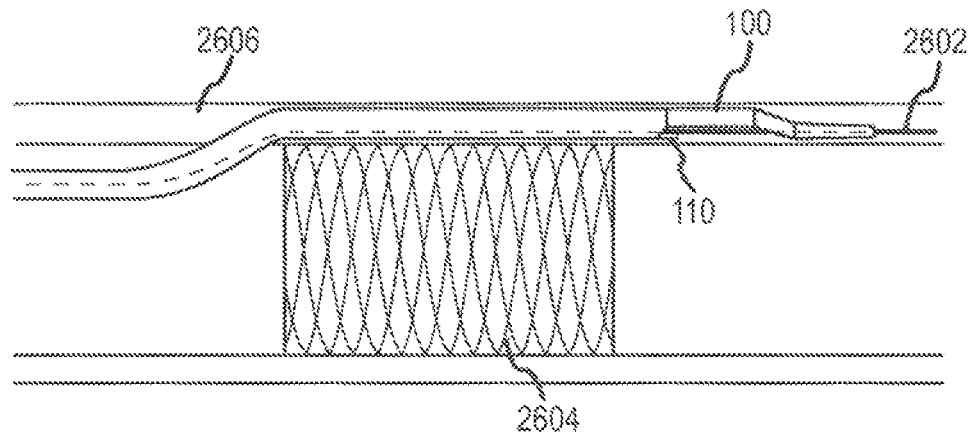
Figure 26D:
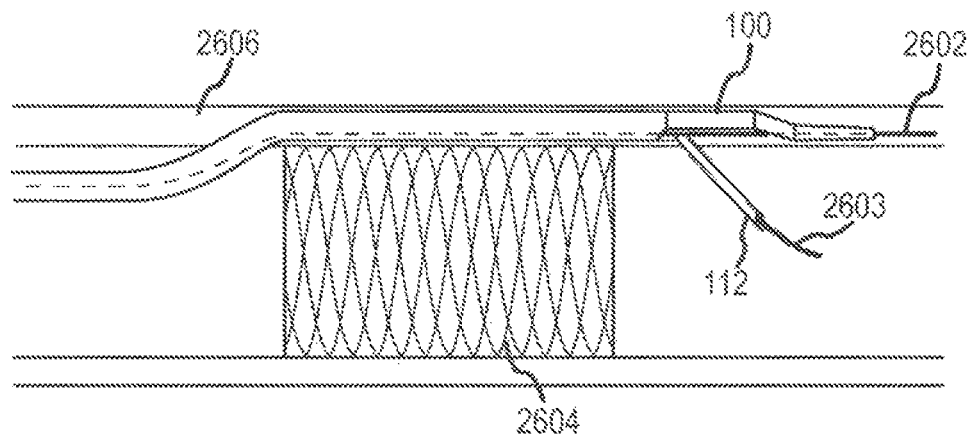

The cannula 1610 could then be moved from a stowed to a ready position and finally fully extended to penetrate the vessel is inner layers as shown in FIG. 26D. In one embodiment, a handle may be configured to transmit force from the proximal end of the catheter to a proximal portion of the reentry cannula 1610 and/or the split tip top 1614. The hard stops 1627 in the split tip bottom 1619 prevent the overextension of the split tip top 1614 and the locking interface between the split tip top and the split tip bottom prevents relative radial motion.

In another embodiment, the split tip top 1614 extends from a direct pushing force of the distal end of the reentry cannula against the distal tip of the split tip top 1614. This movement of the reentry cannula is from an orientation of about parallel to the vessel wall to an orientation between about 0 and about 180 degrees of the vessel wall and more preferably between about 5 to about 90 degrees with respect to the vessel wall and allowing the leading edge of the cannula to penetrate the vessel wall.

In another embodiment, the operator would open the split tip 1602 with a push or other appropriate force applied to its proximal end. The cannula would then be moved from stowed to ready and then launch position as shown in FIG. 26D. This movement of the reentry cannula is from an orientation of about parallel to the vessel wall to an orientation between about 0 and about 180 degrees of the vessel wall and more preferably between about 5 to about 90 degrees with respect to the vessel wall and allowing the leading edge of the cannula to penetrate the vessel wall. The split tip top in its fully extended position provides necessary lateral and axial support to prevent the device from backing out in response to the reentry forces encountered, particularly in the presence of calcified tissue.

Optionally, mechanical advantage components such as levers, manual gearing or electro-mechanical gearing may be incorporated near the proximal end of the catheter and more preferably in the handle such that the reentry cannula may be mechanically controlled through a simple one-handed operation.

In the alternative or in addition to, the activation mechanism may be linked to a simple handle such that the operator either rotates a knob or activates a mechanical or electro-mechanical control element to transition from a ready to an articulated or flexed configuration. The intervention guidewire or another appropriate device may be passed through the shaft lumen and the lumen of the reentry cannula into the true vessel lumen.

During reentry, the vessel wall tends to pull away from a more traditional reentry cannula tip such that penetration will require an increased force application and possible multiple attempts to successfully enter the lumen. The use of a split tip top in its fully extended position provides necessary lateral and axial support to prevent the device from backing out in response to the reentry forces encountered, particularly in the presence of calcified tissue. The use of the split distal tip overcomes this challenge posed by the prior art and allows the operator to reenter at their preferred location easily and repeatedly. Moreover, it is though that the use of the split tip catheter results in more consistent reentry at a location closer to the distal point of the occlusion as compared to the sue of a simple catheter with an extended flexible tip as known in the art. Moreover, the profile of the catheter can be much smaller than reentry devices known in the art since the distal split extending portion can be of sufficient length to support the moment created from the reactionary forces on the catheter during reentry. Known reentry devices incorporate a flexible distal extension that is limited in length due to the larger tip profile. This restriction is necessary to ensure tracking and control through tortuous anatomy. This invention overcomes the problems with the prior art by allowing for a longer and more rigid distal support structure upon reentry while maintaining a substantially reduced profile while traversing through tortuous anatomy.

After the proper reentry of the reentry cannula has been confirmed to be directed towards the true lumen of the vessel, another instrument, e.g., a guidewire, working element, and the like, exits the cannula's distal port and reenters the vessel. Once the intervention guidewire or intervention device is in position, the reentry cannula is retracted back into the cannula exit port of the catheter, the tendon is activated with a pull force to return the extended split tip top to its un-retracted position, and the catheter is removed leaving the interventional device or guidewire in position. Optionally, both the catheter and guidewire may be left in place. Now that the total occlusion is crossed various interventional procedures as known in the art may be performed. For example, a balloon catheter (not shown) may be used to dilate the subintimal space along with possible stent placement (not shown) to provide an alternative lumen through the subintimal space and back into the true vessel to restore adequate blood flow post-procedure.

Figure 17A:
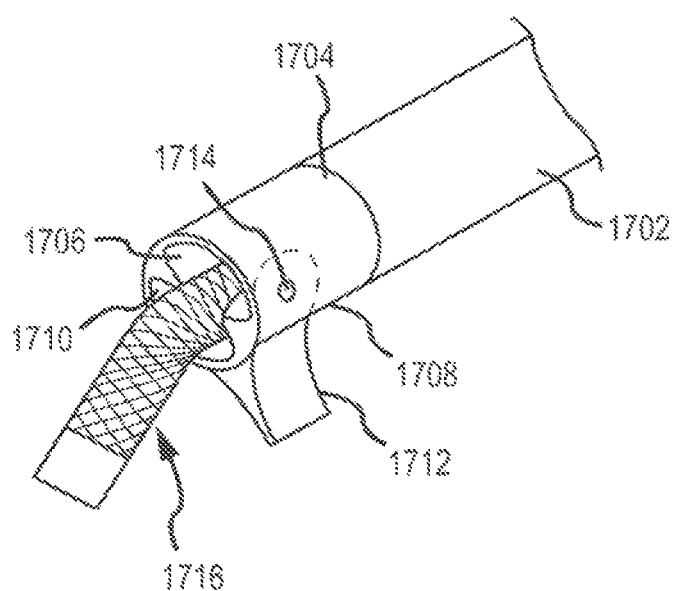
FIG. 17A illustrates a perspective view of the reentry catheter according to another embodiment of the invention.
Figure 17B:
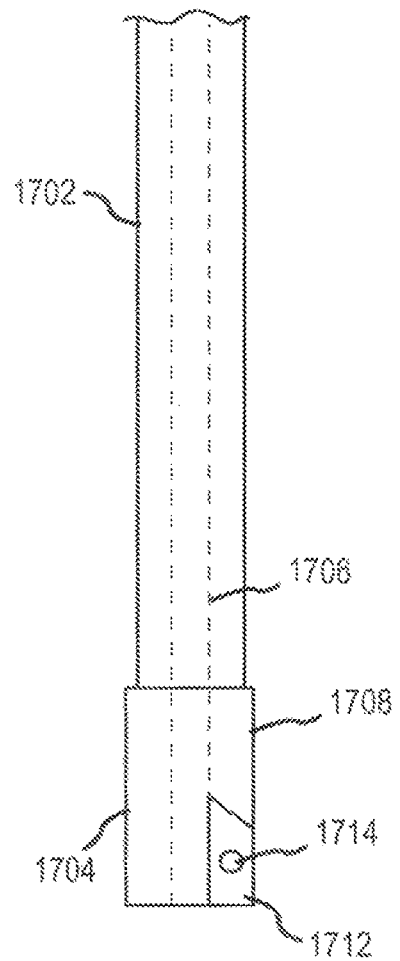
FIG. 17B illustrates an exemplary side view of the reentry catheter illustrated in FIG. 17A.
Figure 17C:
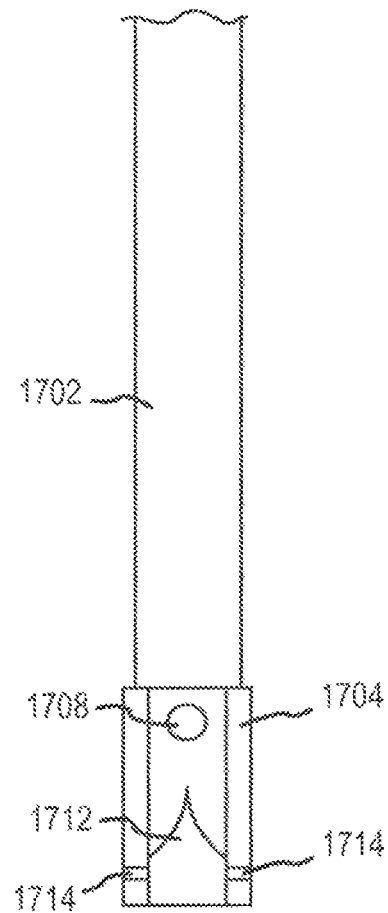
FIG. 17C illustrates an exemplary bottom view of a reentry catheter illustrated as FIG. 17A.

FIG. 17A illustrates a perspective view of the reentry catheter according to another embodiment of the invention. FIG. 17B illustrates an exemplary side view of the reentry catheter illustrated in FIG. 17A. FIG. 17C illustrates an exemplary bottom view of a reentry catheter illustrated in FIG. 17A. FIG. 17D illustrates an end view of a cannula used in the reentry catheter illustrated in FIG. 17A. FIG. 17E illustrates an exemplary side view of the reentry catheter illustrated in FIG. 17A in a deployed position.

Referring to FIGS. 17A-17E, a reentry catheter is generally depicted as reference number 1700. The reentry catheter 1700 includes a catheter body or flexible shaft 1702 connected to a rigid shroud 1704. The shaft 1702 includes at least one lumen 1706, at least one lateral port 1708 and at least one distal port 1710. The catheter can be alternatively configured with an exchange port (not shown), e.g., an exchange port shown in FIGS. 15A-15B. A rotating reentry cutter 1712 is disposed within the rigid shroud 1704 and coupled to the shroud at pivot points 1714. The rotating reentry cutter 1712 is configured to rotate about the pivot axis 1714 from a stowed position within the rigid shroud 1704 to a fully deployed position. The shaft may be constructed of conventional techniques or constructed as described herein. In a preferred embodiment, the shaft includes braided, double braided, or by triplex construction as described herein with reference to FIGS. 11-12.

The distal end of the shaft is connected to the proximal end of the shroud preferably by a laser weld, glue, overmolding or the like as known in the art. There may be more than one lateral port at a distal portion of the shroud 1704.

Optionally, a flexible atraumatic tip may be attached to the distal end of the shroud 1704 preferably by a laser weld, glue, over-molding or the like as known in the art. Alternatively, the shroud 1704 or cover may extend to the catheter distal end and be formed with an atraumatic tip profile. Further, an over molded distal extension (not shown) of the catheter may be incorporated to provide additional support during device orientation and during launch of the rotating reentry cutter. The rotating reentry cutter 1712 is docked within a channel of the rigid shroud, as shown in FIGS. 17B and 17C while traversing through an artery and into or reversed out of the subintimal vessel space. Alternatively, a retractable shroud or cover (not shown) may be used to protect the vessel during catheter transport through the body.

The lumen 1706 may be configured to receive a secondary treatment device 1716, e.g., a flexible crossing support catheter. In a preferred embodiment, the lumen 1706 of the reentry catheter 1700 is sized to accommodate a wide range of guidewire diameters such as guidewire diameters in a range from about 0.01 inches to about 0.04 inches or larger. In an over the wire configuration, the guidewire passes through a lumen of the reentry catheter and passes through the distal end of the catheter as would be the case when the catheter travels through the body and into or out of the subintimal space. Referring to 17A, a support catheter 1716 is shown passing through a lumen of the reentry catheter and passing through the distal end of the catheter as would be the case when the support catheter is used to enter the vessel true lumen. In this embodiment, the lumen of the catheter is designed to allow insertion or integration of a support catheter 1716 at least partially within the catheter inner lumen 1710.

The catheter inner lumen 1706 can also be sized to support a flexible support or crossing catheter, such as a QuickCross® Extreme catheter (The Spectranetics Corporation, Colorado Springs, Colo.). Further, a support catheter with a distal end, a proximal end, a distal port, and at least one lumen is coupled with the reentry catheter and contained within the at least one catheter lumen. In one embodiment, the support catheter is not directly integrated with the reentry catheter. In a preferred embodiment, the support catheter is integrated within the reentry catheter. The support catheter is configured within at least a portion of the distal end of the reentry catheter. Alternatively, the support catheter can extend substantially from the proximal to the distal end of the reentry catheter. The support catheter is configured to slidably move within the at least one lumen of the reentry catheter such that the support catheter can extend beyond at least one port of the reentry catheter. The support catheter is further configured for use with a conventional guidewire or supplemental treatment device within at least one lumen. The rotating reentry cutter 1712 is configured to receive a guidewire 1717 or other supplemental instrument as described herein.

Referring to FIG. 17E, an operator can control or operate the rotating reentry cutter 1712 by holding the catheter in place and by actuating at least one push or pull control element 1718 at a proximal location. In a preferred embodiment, an eccentric force is applied to the rotating reentry cutter 1712 at a distance away from the pivot point 1714 by at least one push or pull member 1718, such that a leading edge 1713 of the rotating of the cutter 1712 moves from a first position contained within the rigid shroud into a second position such that the leading edge in either adjacent to or penetrating vessel layers.

The pull element or actuator 1718 can be a tether, tendon, coil, linkage or other suitable mechanism and is coupled to a portion of the rotating reentry cutter 1712 to apply an eccentric force to the rotating reentry cutter. Preferably two tendons or control elements are attached to the cutter. These control elements can be linked to a handle and actuated through simple one-handed operation such as slides, knobs, and the like as known in the art. Application of an opposite eccentric load causes the rotary reentry cutter to return from the extended or deployed position to a fully retracted position within the rigid distal portion.

In this embodiment, a control element 1718 is used to transmit force from the proximal end of the catheter to a portion of the rotating reentry cutter 1712 at distance from the pivot point 1714. The location of the control element 1718 and the placement of the coupled end are such that a moment is created causing the rotating reentry cutter 1712 to rotate about its pivot joint 1714 from a stowed to a deployed position.

The reentry catheter 1700 is configured to permit a user to cross an obstruction, e.g., a partial or total occlusion, in a subintimal space of a vessel. The catheter 1700 also enables fast and simple true lumen reentry without the need for active visualization, e.g., IVUS visualization. Visualization may be used to assist procedures of the invention, e.g., the visualization may be active or passive. In one embodiment, visualization features or systems are added as described with reference towards U.S. Patent Application Publication No. 2005/0171478, which is hereby incorporated by reference.

At least one marker, e.g., a radiopaque marker, is disposed on the body of the catheter near its distal end or integrated within the body of the catheter. The radiopaque marker is used with standard visualization techniques, e.g., fluoroscopy, to guide the catheter through the body and into position in the subintimal space, to position the lateral port and rotating reentry cutter at a desired location distal to the occlusion, and to determine whether the rotating reentry cutter is in the stowed, ready, or in a fully deployed position.

Optionally, the reentry catheter 1700 includes a reentry cutter 1712 in a stowed position within the rigid shroud 1704 at a location more proximal than shown in FIG. 17A. This more proximal position allows for the leading edge of the cutter 1712 to be stowed near the distal end of the catheter and provides more clearance for supplemental devices, e.g., clearance for the crossing guidewire or a support catheter, such as the QuickCross® Extreme (The Spectranetics Corporation, Colorado Springs, Colo.), through a lateral port.

The advantage of this configuration is that the crossing reentry guidewire is positioned adjacent to the location of the laceration in the subintimal layers created by the rotating reentry cutter. In addition, an internal ramp (not shown), or the like, can be integrated in the distal end of the catheter shaft and the proximal end of the rigid shroud to guide the reentry guidewire or support catheter through a lateral port. The reentry guidewire can also be fed through an exchange port and enter the body of the catheter at a point proximate to the lateral port. Such a configuration may provide the advantage of lower friction forces and improved case-of-use when the reentry catheter is removed from the vessel upon successful crossing of the occlusion. Further, the reentry catheter can be either a traditional over the wire configuration or a rapid exchange configuration. For an over the wire configuration, a signal guidewire can be utilized through the lumen of the catheter. Alternatively, one guidewire can pass through at least one lumen and at least one distal port or at least one exchange port while a second guidewire is used to reenter the true lumen of the vessel from a position distal to the occlusion.

FIG. 17F illustrates a side view of the reentry catheter according to another embodiment of the invention. FIG. 17G illustrates a cutting head of the reentry catheter in FIG. 17F.

Referring to FIG. 17F, the reentry catheter 1700 includes a rotating reentry cutter 1712 rotabably coupled with a pivot 1714 attachment unit. The cutter 1712 has a curvature 1721 on its surface adjacent to the reentry guidewire's lateral exit port that is used to deflect the reentry guidewire in a direction toward the true lumen of the vessel. Specifically the curvature 1721 of the cutting blade can be used as a deflecting guide to direct the reentry crossing guidewire 1725 from a first position within a subintimal space, through the lateral port 1708, along the curvature of the guidewire, through the laceration zone created by the rotating reentry cutter 1712 and into a second position within the vessel true lumen. An internal ramp (not shown) within the distal portion of the catheter can also serve to direct the crossing guidewire through the laceration.

In another embodiment, a guidewire 1723 may be slidably arranged on a curvature 1721 of the rotating cutter 1712. The wire 1723 may be a crossing guidewire and be retained in a channel, retaining rings, or the like, along an edge of the rotating reentry cutter 1712 to serve as a guide to direct the wire 1723 through the laceration created by the rotating reentry cutter when deployed. The reentry guidewire 1723 could be loaded and locked onto the rotating reentry cutter prior to the entry of the catheter into the body.

In another embodiment, at least one marker as described herein, e.g., a radiopaque marker, is dispose don the body of the catheter near its distal end or integrated within the body of the catheter. The radiopaque marker is used with standard visualization techniques, e.g. fluoroscopy, to guide the catheter through the body and into position in the subintimal space, to position the port and rotating reentry cannula at a desired location distal to the occlusion, and to determine whether the rotating reentry cutter is in a stowed, ready, or fully deployed position.

More specifically, as described herein, with reference to FIGS. 26A-26F and supplemented as follows, the crossing of an obstruction in a blood vessel with a reentry catheter in a subintimal space of a vessel is described. In this embodiment, an eccentric load could be applied, as described herein, to rotate the cutter once the reentry catheter is in position within the subintimal space at a location distal to a total occlusion (FIG. 26C). Once the rotating reentry cutter 1712 creates a controlled laceration of the subintimal layers, the crossing guidewire 1723 is released from its locked position and then guided through the laceration into the true lumen of the vessel. The guidewire 1723 may include lubricious coating and have a diameter in a range from about 0.01 inches to about 0.04 inches or larger. In addition, the guidewire may be shapeable, deformable, or have other attributes designed for crossing an occlusion directly or indirectly.

The actuation of the deployment force may be performed through a handle control actuation mechanism near the proximal end of the device as known in the art. Next, an axial pull or push force is applied to the reentry catheter causing the sharp edge of the rotating reentry cutter 1712 to lacerate the subintimal layers of the vessel (FIG. 26D). The length of the laceration can be limited by controls, known in the art, such that the catheter moves a controlled or fixed distance. In one embodiment, a wire, internal support catheter, or interventional device is then deployed through a distal port from within the subintimal space of the vessel to a second location within a true lumen of the vessel. An internal wedge or ramp near the distal end of the reentry catheter can deflect the crossing device towards the true lumen of the vessel. In an alternate embodiment, the crossing device exits a lateral port and is directed towards the true vessel lumen by a variety of means as described herein including the use of a ramp or wedge, guidance along the inner curvature of the rotating cutter device, or retention of the guidewire within a channel or retaining mechanism such that it is directed towards the laceration formed by the rotating reentry cutter and towards the vessel true lumen. Next, the method may include returning the rotating reentry cutter from the second location to the first location and removing the reentry catheter and support catheter (FIG. 17C, closed position), if using, from the vessel (FIG. 26F).

FIG. 18A illustrates a marker band in accordance with another embodiment of the invention. FIG. 18B illustrates a marker band in accordance with another embodiment of the invention.

FIGS. 18A and 18B generally depict a marker or marker band 1802. The marker band 1802 includes is formed as a band and includes a first window cut out 1806 and a second window cut out 1804. This embodiment is directed towards a negative window approach. The first or second cut out window may be configured into any number of geometric configurations, e.g., discrete directional shapes, such as but not limited to letters, e.g., "D", "P", "E", "F"; having a mirror image that differs from the original image; unique shapes such as arrows, multiple rectangular slots; or other directional configurations and combinations thereof. The marker band 1802 is formed from material that is visible under fluoroscopy, e.g., radiopaque materials. More specifically, FIG. 18A illustrates an embodiment with a second pattern cut out 1802 in the form of an arrow 1808. FIG. 18B illustrates an embodiment with a second pattern cut out 1804 in the form of a "D" shape 1810.

Figure 19A:
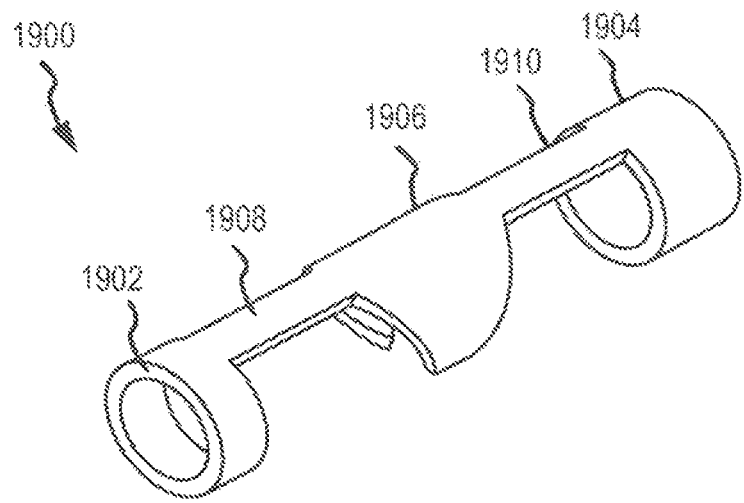
FIG. 19A illustrates a perspective view of a marker band in accordance with another embodiment of the invention.
Figure 19B:
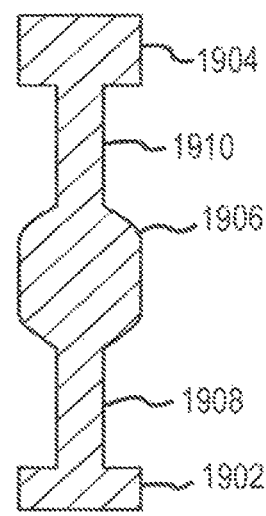
FIG. 19B illustrates a top down view of a marker band in accordance with another embodiment of the invention.
Figure 19C:
FIG. 19C illustrates the marker band of FIG. 19A on a reentry catheter in a first orientation.
Figure 19D:
FIG. 19D illustrates the marker band of FIG. 19B on a reentry catheter in a second orientation.

FIG. 19A illustrates a perspective view of a marker band in accordance with another embodiment of the invention. FIG. 19B illustrates a top down view of a marker band in accordance with another embodiment of the invention. FIG. 19C illustrates a marker band of FIG. 19A on a reentry catheter in a first orientation. FIG. 19D illustrates a marker band of FIG. 19B on a reentry catheter to a second orientation.

Referring to FIGS. 19A and 19B, a marker band is generally depicted as reference number 1900. The marker band 1900 uses a positive approach rather the negative window band approach show in FIGS. 18A-18B. The marker band or marker 1900 is formed from material that is visible under fluoroscopy, e.g., radiopaque materials. In this embodiment, the marker band 1900 is formed with platinum iridium materials. The marker band 1900 is configured to be attached to a distal portion of any catheter described herein. In this embodiment, the marker band 1900 includes a first ring 1902, a second ring 1904, and an oversized central portion 1906 extending only partially in a circular manner. A first longitudinal strip 1908 connects the first ring 1902 to a central portion 1906 and a second longitudinal strip 1910 connects the second ring 1904 to a central portion 1906.

FIG. 19C illustrates a marker band of FIG. 19A on a reentry catheter in a first orientation. FIG. 19D illustrates a marker band of FIG. 19B on a reentry catheter in a second orientation.

Referring to FIGS. 19C-19D, the marker band 1900 is attached to a distal portion of the reentry catheter with a laser tack welding process in a configuration to indicate a specific orientation of a lateral port of the reentry catheter. In a preferred embodiment, the marker band is attached to at the distal end of a rigid shroud of the laser catheter, however, other orientations and locations on the reentry catheter are possible. As shown, the orientation of the lateral port with respect to a vessel wall or other desired trajectory can be determined under a fluoroscopy visualization technique. FIG. 19C shows an anteroposterior (AP) view and in this configuration the marker orientation under fluoroscopy shows a lateral port aligned on top of a vessel such that the cannula (not shown) can be extended into a vessel. FIG. 19D shows that the cannula will extend into a vessel true lumen.

Figure 20A:
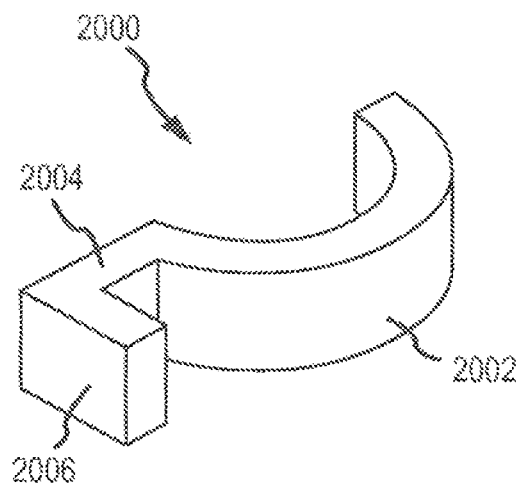
FIG. 20A illustrates a perspective view of a marker band in accordance with another embodiment of the invention.
Figure 20B:
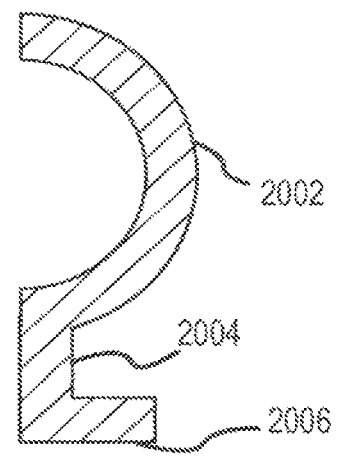
FIG. 20B illustrates a top down view of a marker band in accordance with another embodiment of the invention.
Figure 20C:
FIG. 20C illustrates the marker band of FIG. 20A on a reentry catheter in a first orientation.
Figure 20D:
FIG. 20D illustrates the marker band of FIG. 20B on a reentry catheter in a second orientation.

FIG. 20A illustrates a perspective view of a marker band in accordance with another embodiment of the invention. FIG. 20B illustrates a top down view of a marker band in accordance with another embodiment of the invention. FIG. 20C illustrates a marker band of FIG. 20A on a reentry catheter in a first orientation. FIG. 20D illustrates a marker band of FIG. 20B on a reentry catheter in a second orientation.

Referring to FIGS. 20A and 20B, a marker or marker band is generally depicted as reference number 2000. The marker band 2000 uses a positive approach rather than the negative window band approach show in FIGS. 18A-18B. The marker band 2000 is formed from material that is visible under fluoroscopy, e.g., radiopaque materials. In this embodiment, the marker band 2000 is formed with platinum iridium materials. The marker band 2000 is configured to be attached to a distal portion of any catheter described herein. The marker 2000 includes half circle region 2002, a straight region 2004, and another straight region 2006 at an orthogonal orientation to the straight region 2004.

Referring to FIGS. 20C and 20D, the marker band 2000 is attached to a distal portion of the reentry catheter with a laser welding process in a configuration to indicate a specific orientation of a lateral port of the reentry catheter. In a preferred embodiment, the half circle region 2002 is used as an indicator of the cannula launch direction under fluoroscopy visualization.

As shown, under a fluoroscopy visualization technique the orientation of the lateral port with respect to a vessel wall or other desired trajectory can be determined. FIG. 20C shows an anteroposterior (AP) view and in this configuration the marker orientation under fluoroscopy shows a lateral port aligned on top of a vessel such that the cannula (not shown) can be extended into a vessel. FIG. 20D shows an orientation such that the cannula will extend into a vessel true lumen, e.g., at 30 RAO.

Figure 21A:
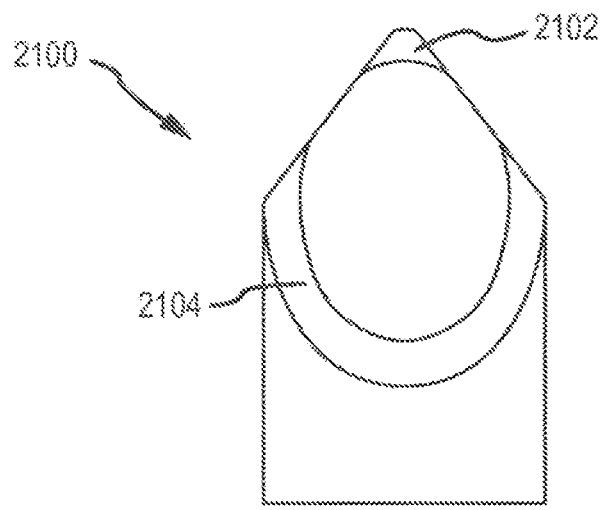
FIG. 21A illustrates a top view of a marker band in accordance with another embodiment of the invention.
Figure 21B:
FIG. 21B illustrates the marker band of FIG. 21A on a reentry catheter in a first orientation.

FIG. 21A illustrates a top view of a marker band in accordance with another embodiment of the invention. FIG. 21B illustrates a marker band of FIG. 21A on a reentry catheter in a first orientation.

Referring to FIGS. 21A and 21B, a marker band or marker is generally depicted as reference number 2100. The marker band 2100 uses a positive approach rather than the negative window band approach show in FIGS. 18A-18B. The marker band 2100 is formed from material that is visible under fluoroscopy, e.g., radiopaque materials. In this embodiment, the marker band 2100 is formed with platinum iridium materials. The marker band 2100 is configured to be attached to a distal portion of any catheter described herein. The marker band or marker 2100 includes a tip portion 2102 and a cut portion 2104. More specifically, the cut portion 2104 is at an angle from about 15 degrees to about 75 degrees into the paper.

The band 2100 is attached to a distal portion of the reentry catheter with a laser welding process in a configuration to indicate a specific orientation of a lateral port of the reentry catheter. As shown, under a fluoroscopy visualization technique the orientation of the lateral port with respect to a vessel wall or other desired trajectory can be determined. FIG. 21B shows an anteroposterior (AP) view and in this configuration the marker orientation under fluoroscopy shows a lateral port aligned on top of a vessel such that the cannula (not shown) can be extended into a vessel.

Figure 22A:
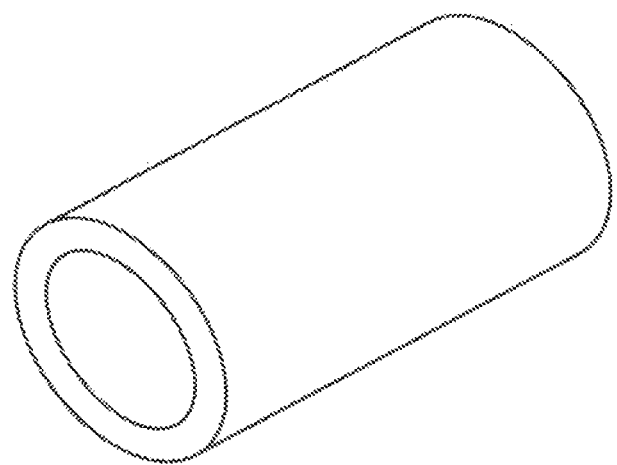
FIG. 22A illustrates a top view of a marker band in accordance with another embodiment of the invention.
Figure 22B:
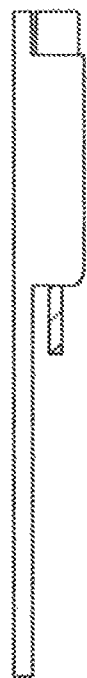
FIG. 22B illustrates the marker band of FIG. 22A on a reentry catheter in a first orientation.

FIG. 22A illustrates a top view of a marker band in accordance with another embodiment of the invention. FIG. 22B illustrates a marker band of FIG. 22A on a reentry catheter in a first orientation.

Referring to FIGS. 22A and 22B, a marker band or marker is generally depicted as reference number 2200. The marker band 2200 uses a positive approach rather than the negative window band approach show in FIGS. 18A-18B. The marker band 2200 is formed from material that is visible under fluoroscopy, e.g., radiopaque materials. In this embodiment, the marker band 2200 is formed with platinum iridium materials. The marker band 2200 is configured to be attached to a distal portion of any catheter described herein. The marker band 2200 includes an oval geometry.

The band 2200 is attached to a distal portion of the reentry catheter with a laser welding process in a configuration to indicate a specific orientation of a lateral port of the reentry catheter. As shown, under a fluoroscopy visualization technique the orientation of the lateral port with respect to a vessel wall or other desired trajectory can be determined. FIG. 22B, shows an anteroposterior (AP) view and in this configuration the marker orientation under fluoroscopy shows a lateral port aligned on top of a vessel such that the cannula (not shown) can be extended into a vessel.

FIG. 23A illustrates a top view of marker band in accordance with another embodiment of the invention. FIG. 23B illustrates the marker band of FIG. 22A on a reentry catheter in a first orientation. FIG. 23C illustrates the marker band of FIG. 22A on a reentry catheter in a second orientation. FIG. 23D illustrates the marker band of FIG. 22A on a reentry catheter in a third orientation.

Referring to FIG. 23A-23D, the marker band or marker is generally depicted as reference number 2300. The marker band 2300 uses a positive approach rather than the negative window band approach shown in FIGS. 18A-18B. The marker band 2300 is formed from material that is visible under fluoroscopy, e.g., radiopaque materials. In this embodiment, the marker band 2300 is formed with platinum iridium materials. The marker band 2300 is configured to be attached to a distal portion of any catheter described herein. The marker band 2300 includes two vertical slots 2302 and 2304, respectively.

The band 2300 is attached to a distal portion of the reentry catheter with a laser welding process in a configuration to indicate a specific orientation of a lateral port of the reentry catheter. Referring now to FIG. 23B, the guidewire 2306 of the device is on the left and in this orientation the cannula (or lateral port) would be pointing into the page as indicated by the arrow. Referring now to FIG. 23C, the guidewire 2304 of the device is on the right and in this orientation the cannula (or lateral port) would be pointing out of the page as indicated by the arrow. Referring now to FIG. 23D, the guidewire 2304 of the device is on the right and in this orientation the cannula (or lateral port) is not aligned.

Figure 23E:
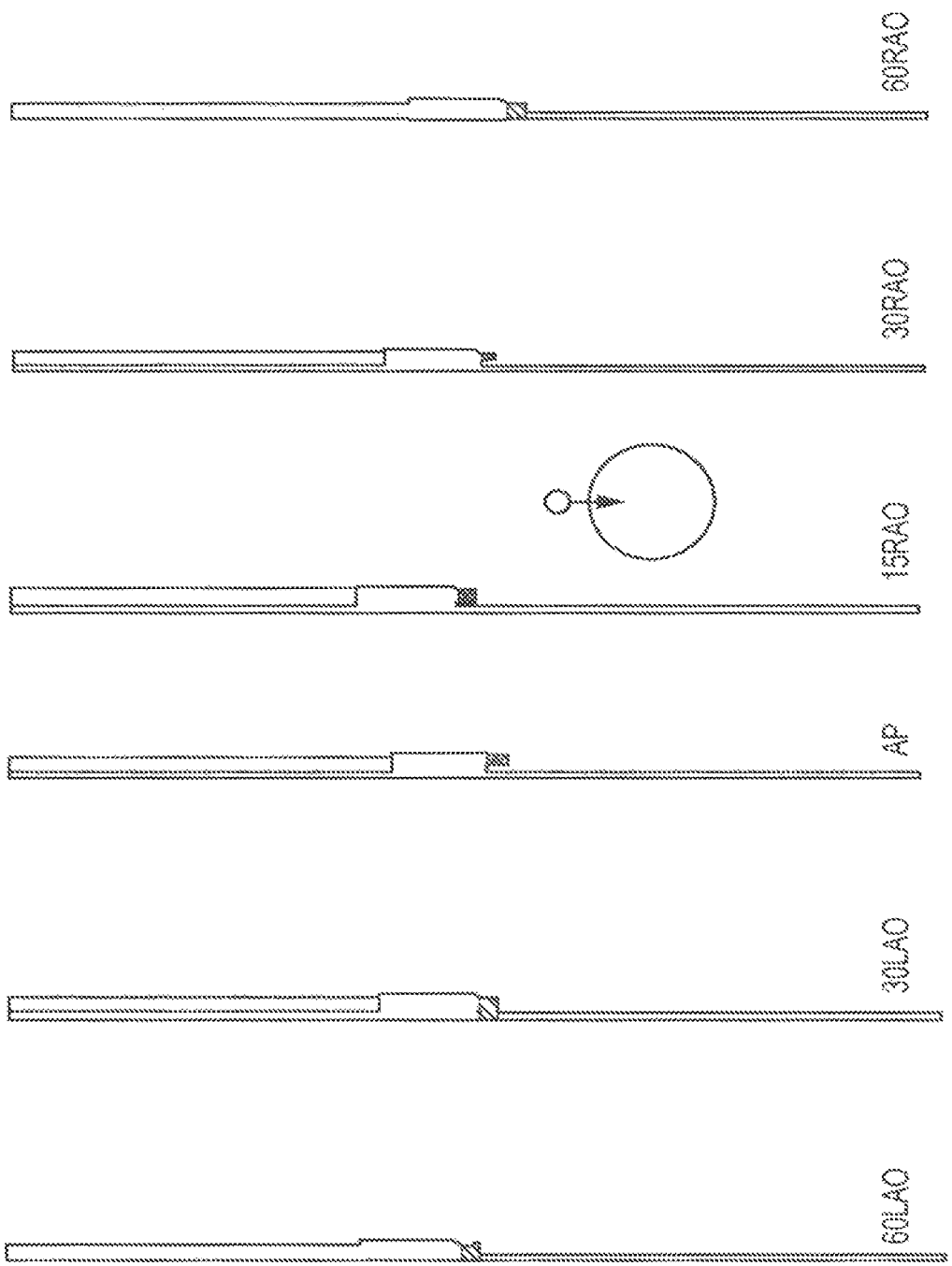
FIG. 23E illustrates a catheter with the marker band shown in FIG. 23A in various orientation from 60 left anterior oblique (LAO) to 60 right anterior oblique (RAO).

FIG. 23E illustrates a catheter with a marker band shown in FIG. 23A in various orientations from 60 left anterior oblique (LAO) to 60 right anterior oblique (RAO). Referring to FIG. 23E, the reentry catheter is correctly oriented at 15 RAO. In this 15 RAO orientation the vertical windows appear to be most visible and the device is directly on top of the vessel. The cannula would be pointed into the page as the guidewire is on the left.

FIG. 23F illustrates a catheter with a marker band shown in FIG. 23A on a reentry catheter in various orientations from 60 left anterior oblique (LAO) to 60 right anterior oblique (RAO). Referring to FIG. 23F, the reentry catheter is correctly oriented at the AP projection. In this AP orientation the vertical windows appear to be most visible and the device is directly on the bottom of the vessel. The cannula would be pointed out of the page as the guidewire is on the right.

FIG. 24A illustrates a top view of a marker band in accordance with another embodiment of the invention. FIG. 24B illustrates the marker band of FIG. 24A on a reentry catheter in a first orientation. FIG. 24C illustrates the marker band of FIG. 24A on a reentry catheter in a second orientation. FIG. 24D illustrates the marker band of FIG. 24A on a reentry catheter in a third orientation.

Referring to FIG. 24A-24D, the marker band or marker is generally depicted as reference number 2400. The marker band 2400 uses a negative approach. The marker band 2400 is formed from material that is visible under fluoroscopy, e.g., radiopaque materials. In this embodiment, the marker band 2400 is formed with platinum iridium materials. The marker band 2400 is configured to be attached to a distal portion of any catheter described herein. The marker band 2400 includes two "D" type shape 2402.

The band 2400 is attached to a distal portion of the reentry catheter with a laser welding process in a configuration to indicate a specific orientation of a lateral port of the reentry catheter. Referring now to FIG. 24B, a clear "D" type shape is shown and the guidewire 2404 of the device is on the left and in this orientation the cannula (or lateral port) would be pointing into the page as indicated by the arrow. Referring now to FIG. 24C, a reverse D type shape is shown and the guidewire 2404 of the device is on the right and in this orientation the cannula (or lateral port) would be pointing out of the page as indicated by the arrow. Referring now to FIG. 24D, the guidewire of the device is on the right and in this orientation the cannula (or lateral port) is not aligned as indicated by the arrow.

Figure 24E:
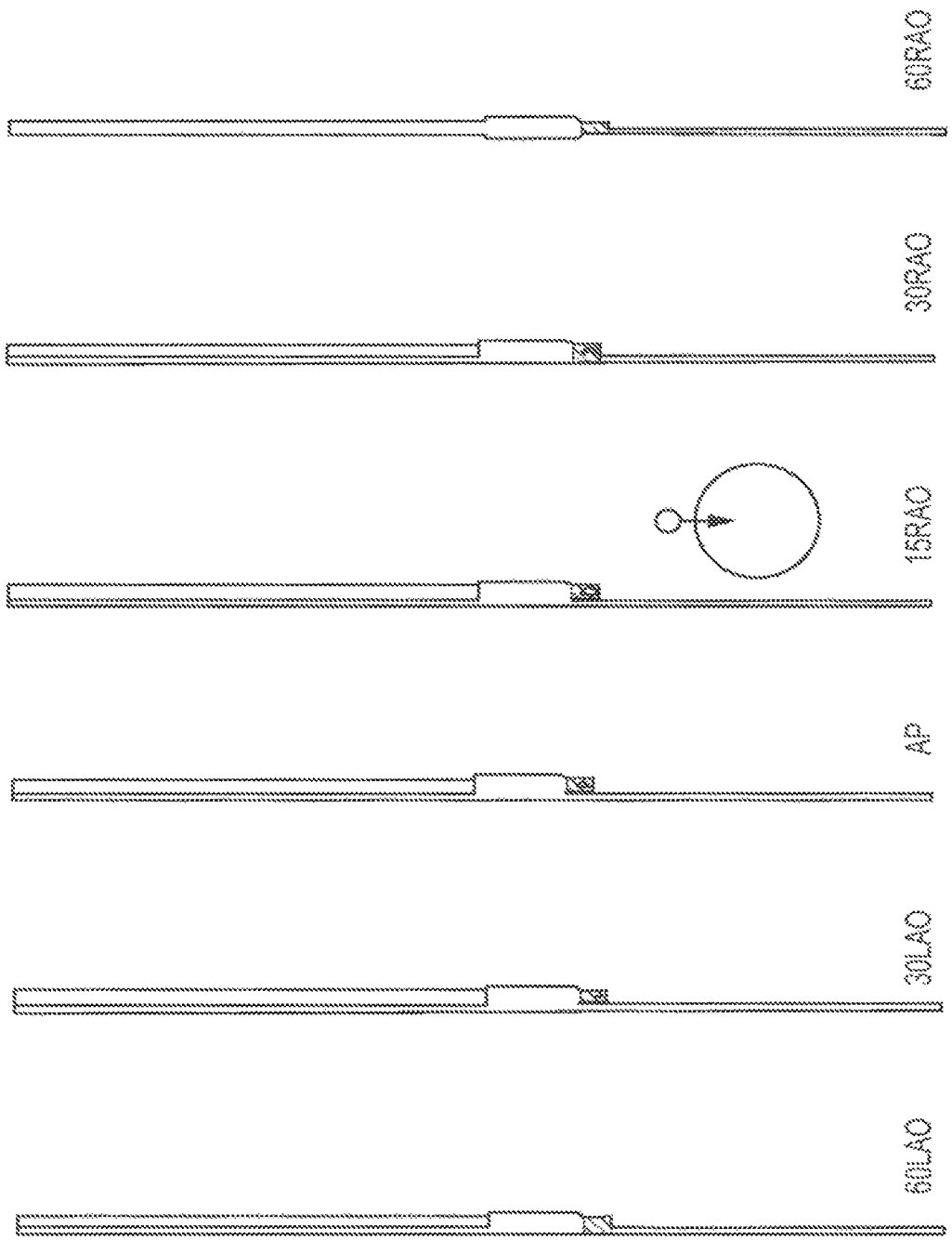
FIG. 24E illustrates a catheter with the marker band shown in FIG. 23A in various orientations from 60 left anterior oblique (LAO) to 60 right anterior oblique (RAO).

FIG. 24E illustrates a catheter with the marker band shown in FIG. 24A in various orientation from 60 left anterior oblique (LAO) to 60 right anterior oblique (RAO). Referring to FIG. 24E, the reentry catheter is correctly oriented at 15 RAO. In this 15 RAO orientation the "D" type shape appears to be most visible and the device is directly on top of the vessel. The cannula would be pointed into the page as the guidewire is on the left.

Figure 24F:
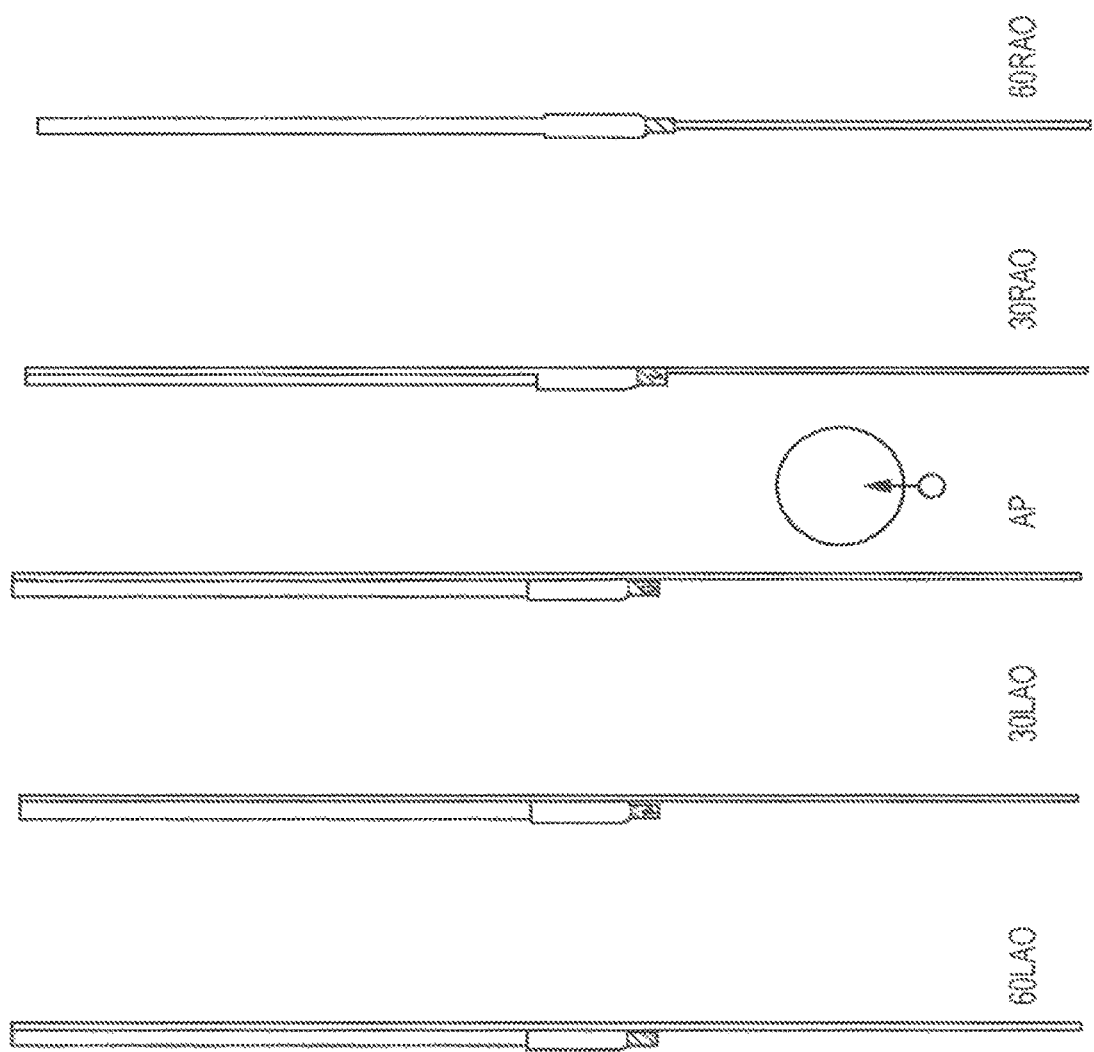
FIG. 24F illustrates a catheter with the marker band shown in FIG. 23A on a reentry catheter in various orientations from 60 left anterior oblique (LAO) to 60 right anterior oblique (RAO)

FIG. 24F illustrates a catheter with the marker band shown in FIG. 24A on a reentry catheter in various orientations from 60 left anterior oblique (LAO) to 60 right anterior oblique (RAO). Referring to FIG. 24F, the reentry catheter is correctly orientated at the AP projection. In this AP orientation the "D" type shape appears to be most visible and the device is directly on the bottom of the vessel. The cannula would be pointed out of the page as the guidewire is on the right.

FIG. 25A illustrates a top view of a marker band in accordance with another embodiment of the invention. FIG. 25B illustrates the marker band of FIG. 25A on a reentry catheter in a first orientation. FIG. 25C illustrates the marker band of FIG. 25A on a reentry catheter in a second orientation. FIG. 25D illustrates the marker band of FIG. 25A on a reentry catheter in a third orientation.

Referring to FIG. 25A-25D, the marker band or marker is generally depicted as reference number 2500. The marker band 2500 uses a negative approach. The marker band 2500 is formed from materials that are visible under fluoroscopy, e.g., radiopaque materials. In this embodiment, the marker band 2500 is formed with platinum iridium materials. The marker band 2500 is configured to be attached to a distal portion of any catheter described herein. The marker band 2400 includes a first arrow region 2502 and a second arrow region 2504.

The band 2500 is attached to a distal portion of the reentry catheter with a laser welding process in a configuration to indicate a specific orientation a lateral port of the reentry catheter. Referring now to FIG. 25B, a first arrow region 2502 and a second arrow region 2504 is shown and the guidewire of the device could either be on the left or right of the device due to the symmetry of the first arrow region 2502 and the second arrow region 2504. The orientation of the cannula (or lateral port) would be pointing into the page or out of the page as indicated by the arrows. Referring now to FIG. 25C, a second arrow 2504 is clearly shown and a first arrow 2502 is partially shown. The cannula is misaligned in this orientation and the cannula (or lateral port) is pointing in a direction as indicated by the arrow. Referring now to FIG. 25D, the guidewire of the device is on either the left or right of the device and the cannula (or lateral port) is pointing in a direction as indicated by the arrow.

FIG. 25E illustrates a catheter with a marker band shown in FIG. 25A in various orientation from 60 left anterior oblique (LAO) to 60 right anterior oblique (RAO). Referring to FIG. 25E, the reentry catheter is correctly oriented at 10 RAO. In the 10 RAO orientation, the first arrow 2502 and second arrow 2504 are most visible and the device is directly on top of the vessel. The cannula would be pointed into the page as the guidewire is on the left.

Figure 25F:
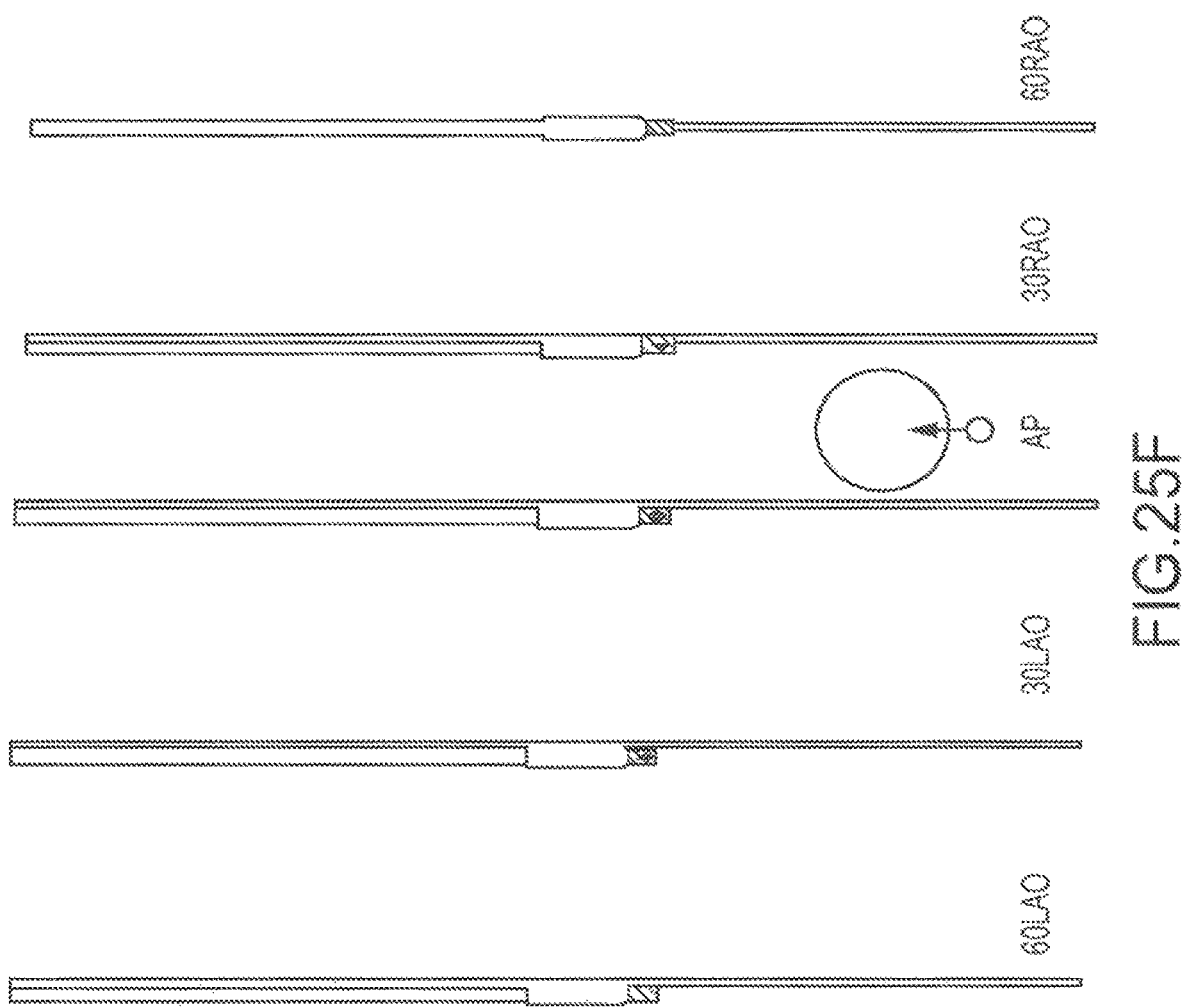
FIG. 25F illustrates catheter with the marker band shown in FIG. 25A on a reentry catheter in various orientation from 60 left anterior oblique (LAO) to 60 right anterior oblique (RAO).

FIG. 25F illustrates a catheter with the marker band shown in FIG. 25A on a reentry catheter in various orientations from 60 left anterior oblique (LAO) to 60 right anterior oblique (RAO). Referring to FIG. 25F, the reentry catheter is correctly oriented at the AP projection. In this AP orientation the first arrow 2502 and second arrow 2504 are most visible and the device is directly on the bottom of the vessel. The cannula would be pointed out of the page as the guidewire is on the right.

FIGS. 26A-26F illustrates an exemplary method for using a medical device of FIG. 1.

Referring to FIGS. 26A-26F, a guidewire 2602 is advanced to an occlusion 2604 in an attempt by the physician to cross the occlusion to use conventional interventional devices such as laser atherectomy catheters, balloons, drug delivery devices, stents and the like. This advancement of the guidewire 2602 is done in accordance with techniques known in the field of cardiology, interventional radiology and the like. In some instances, the physician is unable to cross through the lesion from the proximal lesion end to a point distal to the lesion through the true lumen of the vessel. In these instances, as shown in FIG. 26A, the guidewire 2602 may unintentionally or intentionally enter the subintimal space 2606 after reaching the total occlusion 2604. The guidewire 2602 may include lubricious coating and have a diameter in a range from about 0.01 inches to about 0.04 inches or larger. In addition, the guidewire 2602 may be shapeable, deformable, or have other attributes designed for crossing an occlusion directly or indirectly.

Referring to FIG. 26B, after the guidewire 2602 has reached the subintimal space 2606 a reentry catheter 100 is advanced over an RX port 114 into the subintimal space 2606. Of course, any catheter described herein may also be used and reference to catheter 100 is done merely out of convenience. Next, the catheter 100 is advanced to a position distal to the occlusion 2604.

Referring to FIG. 26C, the catheter 100 is oriented to a position such that the lateral port 110 is distal to the occlusion 2604. In a preferred embodiment, the orientation of the catheter 100 may be conducted with utilization of the marker band cut outs or windows 132, 134 on the marker band as described previously. For example, in a preferred embodiment the catheter is configured such that different views of fluoroscopic images enable the operator to align the lateral port 110 so that the cannula 112 or other instrument, e.g., guidewire, working element, and the like, is aligned with a true lumen of the vessel. It is noted that other active or passive visualization techniques as known in the art may also be utilized to orient the lateral port 110 with a true lumen.

Moreover, in a preferred embodiment, the molded tip 118 is configured to provide stability and alignment for reentry position along the arc length of the artery. For example, the lateral extension of the molded tip is configured to provide stability during the initial orientation of the device over the central arc of the lesion. When the device rotates into position, the natural tendency will be to fall into the contour of the artery. Therefore the lateral port will naturally either be oriented into the true lumen or oriented about 180 degree from the true lumen. The markers, e.g., radiopaque markers, are configured to permit an operator to rotate the device if needed prior to launching the cannula into the vessel for reentry.

In another embodiment, the catheter includes a cannula, e.g., a straight cannula, which is configured to exit the lateral port at an angle in a range from about 5 degrees to about 90 degrees, more preferably at an angle in a range from about 5 degrees to about 45 degrees. Exiting the lateral port at an angle as described allows for less force to be applied on the catheter. A more orthogonal approach relies on the hoop strength of the vessel to support reentry forces. During penetration, the vessel wall will pull away from the cannula tip such that penetration will require increased force application and possible multiple attempts to successfully enter the lumen.

By entering the arterial wall at a lower approach angle, the longitudinal strength of the vessel wall supports penetration creating a lateral dissection plane through the vessel wall. This results in less resistance to penetration and more consistent reentry at the desired location. Therefore, it is believed that the angle of cannula entry in combination with the tensile strength of the shaft obtained from tri-coil construction allows the operator to re-enter the true lumen easily and repeatably at their preferred location. Moreover, it is thought that the lower approach angle results in more consistent reentry at a location closer to the distal point of the occlusion as compared to the orthogonal approach through the use of a curved cannula with or without a curved shroud.

Moreover, incorporation of a tricoil component to the design improves the pushability and trackability of the device through the subintimal space and through the entry and reentry processes. Specifically, the tricoil member improves torque transmission from the proximal to the distal end of the device while retaining the device is overall flexibility. The improved torque control compared to prior art allows the operator to control the orientation of the distal end of the catheter with increase accuracy and precision.

Figure 26E:
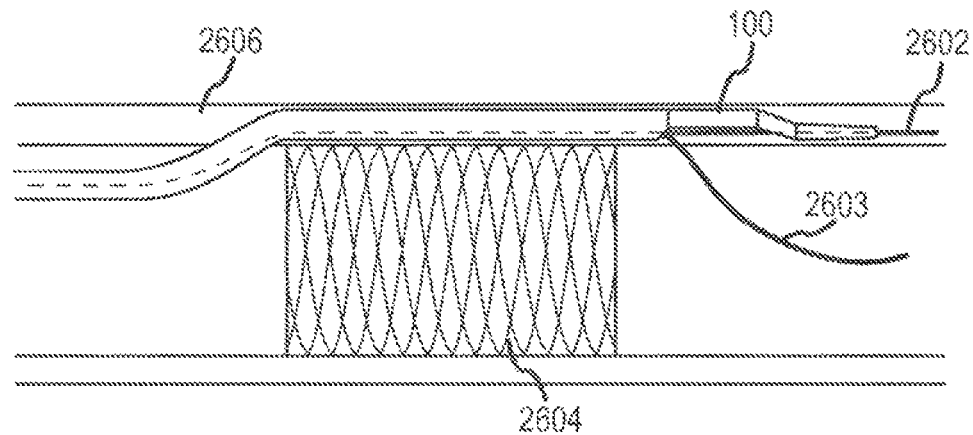
Figure 26F:
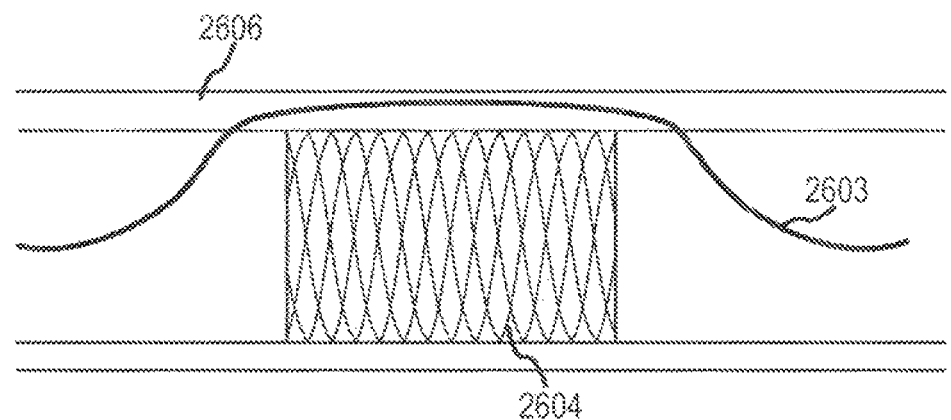

Referring to FIGS. 26D-26F, after the orientation of the lateral port 110 has been confirmed to be directed towards the true lumen of the vessel, a cannula 112 or other instrument, e.g., guidewire, working element, and the like, exits the lateral port 110 and reenters the vessel. A second guidewire 2603 is configured to exit the lumen of the cannula 112 and into the true lumen of the vessel. The cannula is retracted back into the lateral port 110 of the catheter 100 and the catheter and guidewire 2606 are removed as shown in FIG. 26F. Optionally, both the catheter (100) and guidewire 2602 may be left in place. Now that the total occlusion is crossed various interventional procedures as known in the art may be performed. For example, a balloon catheter (not shown) may be used to dilate the subintimal space along with possible stent placement (not shown) to provide an alternative lumen through the subintimal space and back into the true vessel to restore adequate blood flow post-procedure.

EXAMPLES

Without intending to limit the scope of the invention, the following examples illustrate how various embodiments of the invention may be made and/or used.

Example 1

Example 1 illustrates the manufacture of a reentry device according to an aspect of the invention. Referring to FIG. 27, the reentry catheter is generally depicted as reference number 2700. A custom manufactured tri-coil shaft 2702 was obtained from Heraeus Medical Components of St. Paul, Minn. The tri-coil shaft has an overall outer diameter of about 0.05 inches, an inner overall diameter of about 0.04 inches and an overall length of about 48 inches. The tri-coil shaft includes three separate coil windings of stainless steel flat wire. The outer winding and innermost windings are manufactured to a specification of 6-Filar close would, left-hand sided and the inner windings are manufactured at a specification of 6-Filar close wound right-hand sided. The tri-coil shaft is covered or jacketed with PEBAX through a lamination process. The tri-coil shaft has a lumen of about 0.04 inches diameter that extends from a proximal end to a distal end. A polyimide tube 2704 is coupled to the PEBAX jacket using a PEBAX lamination process similar to that used for jacketing the tri-coil shaft. The polyimide tube was obtained from MicroLumen, Inc. of Tampa, Fla. and has a dimension of about 12 inches in length, about 0.026 inches in outside diameter, and about 0.002 inches in wall thickness. The PEBAX jacket and polyimide tube is coated with hydrophilic coating using a combination of reagents obtained from Surmodics of Eden Praire, Minn. The coating was done through a simple immersion process.

Next, a stainless steel structure 2706 was fabricated with dimensions of about 0.26 inches in length and 0.06 inches in outer diameter. The structure includes a side port of about 0.10 inches in length with a nominal width of about 0.040 inches. In addition, the lumen of the stainless structure includes a ramp at an angle of about 25 degrees configured to deflect the cannula 2710 and guidewire 2712 out a lateral port 2714.

A cylindrical platinum iridium marker band 2716 was manufactured by Johnson Matthey from the United Kingdom. This marker band has an outer diameter of about 0.04 inches, an inner diameter of about 0.030 inches, and an overall length of about 0.075 inches. A first rectangular cutout window with rounded corners is centered along one circumferential side of the marker band with a length of about 0.045 inches and width of about 0.03 inches. A second cutout pattern comprised of two narrower rectangular windows is centered at an orientation of 180 degrees relative to the center of the first cutout window. The narrower rectangular windows have rounded corners and dimensions of about 0.045 inches in length and 0.01 inches in width. A solid band of material with a width of about 0.010 inches separates the two narrower rectangular window components. The marker band is laser tack welded to the distal end of the rigid shroud in four places at an orientation of about 90 degrees between each weld. The distal end of the tri-coil shaft is laser welded to the proximal end of the rigid shroud through four tack welds also oriented about 90 degrees apart around the circumference of the shaft.

A custom PEBAX micro-molded end portion 1818 having a length of 0.58 inches was obtained from Mikrotech, LLC, of Diablo Calif. This molded end portion is micro-molded over the distal portion of the shroud which contains the laser tack welded marker band. A second platinum iridium marker 2720 is molded into the distal tip of the molded end portion such that the second marker is integral to and completely encapsulated within the molded end portion to provide reference to the placement of the exchange guidewire within the tip during the reentry procedure. The second marker is 0.19 inches from the end of distal end of the end portion. The most distal end of the molded end portion is designed with a radiused, atraumatic profile.

A cannula 2710 made of nitinol material with an inner diameter of 0.023 inches and a wall thickness of 0.0025 inches was fabricated. The length of the cannula is 60 inches. The distal end of the cannula is cut to an angle of 25 degrees to provide a sharp surface. The distal face of the cannula is star point ground to a minimum of 40% and a maximum of 60% of bevel length. The cannula lumen and the exchange port lumen are configured to accept wires up to 0.018 inches in diameter. A handle (not shown) is attached to the proximal end of the welded coil assembly. The handle contains luers and attachments for flushing and attachments for the cannula.

Example 2

Figure 28:
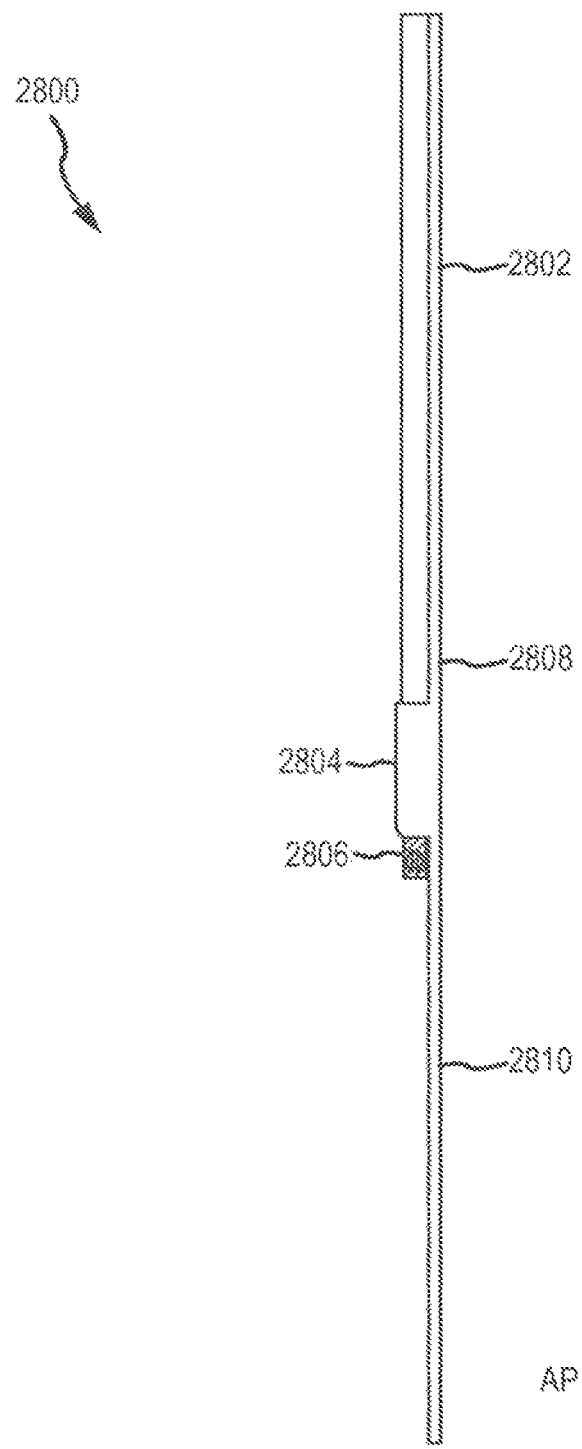
FIG. 28 illustrates a photograph of a reentry device manufactured as described in Example 2.

Example 2 illustrates the manufacture of a reentry device according to an aspect of the invention. Referring to FIG. 28, the reentry catheter is generally depicted as reference number 2800. The device is constructed in the same manner as described for Example 1 using the same components including a PEBAX jacketed tri-coil shaft 2802, rigid shroud 2804 with a lateral port and internal deflection ramp, a cylindrical marker band 2806, and a polyimide exchange port 2808 with the exception that a molded end portion is not overmolded on the distal end of the rigid shroud. Referring to FIG. 28, there are a number of visualization techniques that may be used with this catheter. Here a fluoroscopy visualization method was used. The exchange guidewire 2810 and/or marker band 2806 can be used as a visual cue regarding the orientation of the lateral port with respect to the true vessel lumen. In this configuration, the reentry catheter is shown in the correct orientation for deployment of the cannula into the vessel true lumen. Conversely, if the guidewire was shown on the left hand side of the rigid shroud, then the catheter must be rotated about 180 degrees prior to cannula deployment.

The inventions and methods described herein can be viewed as a whole, or as a number of separate inventions that can be used independently or mixed and matched as desired. All inventions, steps, processes, devices, and methods described herein can be mixed and matched as desired. All previously described features, functions, or inventions described herein or by reference may be mixed and matched as desired.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A rapid exchange catheter system, comprising:
    a shaft having an inner lumen, an exchange port lumen and an exchange port fluidly coupled with the exchange port lumen, the exchange port arranged on a distal portion of the shaft, the inner lumen configured to receive a first wire, and the exchange port lumen and the exchange port configured to receive a wire; and
    a rigid shroud coupled to the distal portion of the shaft, the rigid shroud comprising a first lumen, a second lumen, and a lateral port fluidly coupled with the second lumen of the shroud and the inner lumen of the shaft, the second lumen and the lateral port configured to receive the first wire, the first lumen comprising a proximal port and a distal port in the rigid shroud, wherein the exchange port is disposed proximally of the lateral port and the proximal port is disposed distally of the lateral port;
    wherein, as viewed from a distal end view of the rapid exchange catheter system, the exchange port is disposed radially exterior of the rigid shroud.

2. The rapid exchange catheter system of claim 1, further comprising a cannula disposed within the second lumen, the cannula configured to extend from the lateral port and receive the first wire.

3. The rapid exchange catheter system of claim 1, wherein the exchange port is disposed proximally relative to the rigid shroud.

4. The rapid exchange catheter system of claim 1, wherein the rigid shroud further comprises a wire guide configured to receive the second wire, wherein the wire guide is adjacent the proximal port of the first lumen.

5. The rapid exchange catheter system of claim 4, wherein the lateral port is disposed proximally relative to the wire guide.

6. The rapid exchange catheter system of claim 5, wherein, as viewed from the end view of the rapid exchange catheter system, the lateral port, the exchange port, and a center of the rigid shroud define an angle, the angle having a vertex at the center of the rigid shroud, a first side intersecting the center of the rigid shroud and the lateral port, and a second side intersecting the center of the rigid shroud and a center of the exchange port, and the angle is less than 180 degrees.

7. The rapid exchange catheter system of claim 1, further comprising a marker band carried by the rigid shroud.

8. The rapid exchange catheter system of claim 1, wherein the shaft comprises three coils.

9. The rapid exchange catheter system of claim 8, wherein the three coils are oppositely wound.

10. The rapid exchange catheter system of claim 1, wherein, as viewed from the end view of the rapid exchange catheter system, the lateral port, the exchange port, and a center of the rigid shroud define an angle, the angle having a vertex at the center of the rigid shroud, a first side intersecting the center of the rigid shroud and the lateral port, and a second side intersecting the center of the rigid shroud and a center of the exchange port, and the angle is less than 180 degrees.

11. A method of using a rapid exchange catheter system, the method comprising:
    advancing a first wire into a subintimal space within a blood vessel;
    advancing the rapid exchange catheter system over the first wire into the subintimal space, wherein the rapid exchange catheter system comprises:
        a shaft having an inner lumen, and exchange port lumen and an exchange port fluidly coupled with the exchange port lumen, the exchange port arranged on a distal portion of the shaft, the inner lumen configured to receive a wire, and the exchange port lumen and the exchange port receiving the first wire; and
        a rigid shroud coupled to the distal portion of the shaft, the rigid shroud comprising a first lumen, a second lumen, and a lateral port fluidly coupled with the second lumen and the inner lumen of the shaft, the second lumen and the lateral port configured to receive the wire, the first lumen comprising a proximal port and a distal port in the rigid shroud, wherein the first lumen is configured to receive the first wire, wherein the exchange port is disposed proximally of the lateral port and the proximal port is disposed distally of the lateral port;
        wherein, as viewed from a distal end view of the rapid exchange catheter system, the exchange port is disposed radially exterior of the rigid shroud;
    advancing the wire through inner lumen of the shaft and the second lumen of the rigid shroud; and
    advancing the wire through the lateral port of the rigid shroud into a lumen of the blood vessel.

12. The method of claim 11, further comprising advancing a cannula a predetermined distance out of the lateral port.

13. The method of claim 11, further comprising actuating an actuator to mechanically advance a cannula a predetermined distance out of the lateral port.

14. The method of claim 11, wherein the exchange port and the lateral port are disposed distally relative to an occlusion in the lumen of the blood vessel as a result of advancing the rapid exchange catheter system over the first wire.

15. The method of claim 11, wherein, as viewed from the end view of the rapid exchange catheter system, the lateral port, the exchange port, and a center of the rigid shroud define an angle, the angle having a vertex at the center of the rigid shroud, a first side intersecting the center of the rigid shroud and the lateral port, and a second side intersecting the center of the rigid shroud and a center of the exchange port, and the angle is less than 180 degrees.

16. The method of claim 11, wherein the exchange port is disposed proximally relative to the rigid shroud.

17. The method of claim 11, wherein the rigid shroud further comprises a wire guide, wherein the wire guide is adjacent the proximal port of the first lumen, and further comprising the step of receiving the first wire in the wire guide.

18. The method of claim 17, wherein the lateral port is disposed proximally relative to the wire guide and distally relative to the exchange port.

* * * * *